US008155757B1

(12) United States Patent
Neisz et al.

(10) Patent No.: US 8,155,757 B1
(45) Date of Patent: Apr. 10, 2012

(54) CUFF ELECTRODE HAVING TUBULAR BODY WITH CONTROLLED CLOSING FORCE

(75) Inventors: Hans Neisz, Coon Rapids, MN (US); Ralph Cardinal, White Bear Lake, MN (US); Jason Shiroff, Minneapolis, MN (US); Jason John Skubitz, Arden Hills, MN (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 862 days.

(21) Appl. No.: 12/181,214

(22) Filed: Jul. 28, 2008

Related U.S. Application Data

(60) Provisional application No. 61/036,429, filed on Mar. 13, 2008, provisional application No. 60/952,219, filed on Jul. 26, 2007.

(51) Int. Cl.
 *A61N 1/04* (2006.01)
(52) U.S. Cl. .................................................. 607/118
(58) Field of Classification Search .................... 607/118
See application file for complete search history.

(56) References Cited

U.S. PATENT DOCUMENTS

2006/0116739 A1* 6/2006 Betser et al. .................... 607/48

OTHER PUBLICATIONS

Rozman, J. et al., "Multielectrode Spiral Cuff for Selective Stimulation of Nerve Fibres", Journal of Medical Engineering and Technology, vol. 16, No. 5,(1992), pp. 194-203.

Rozman, Janez et al., "Recording of Electroneurograms from the Nerves Innervating the Pancreas of a Dog", Journal of Neuroscience Methods, vol. 112,(2001), pp. 155-162.

Rozman, J. et al., "Recording of ENGs from the Nerves Innervating the Pancreas of a Dog During the Intraveneous Glucose Tolerance Test", Physiol. Meas., vol. 23(4),(2002), pp. 695-705.

Rozman, Janez et al., "Stimulation of Nerves Innervating the Dog's Pancreas", Artificial Organs, vol. 26(3),(2002), pp. 241-243.

Sweeney, James D., et al., "An Asymmetric Two Electrode Cuff for Generation of Unidirectionally Propagated Action Potentials", IEEE Transactions on Biomedical Engineering, vol. BME-33 No. 6,(Jun. 1986), pp. 541-549.

* cited by examiner

*Primary Examiner* — Eric D. Bertram
(74) *Attorney, Agent, or Firm* — Craig Hoersten; Christopher S. L. Crawford; Peter R. Lando

(57) ABSTRACT

Nerve cuff electrodes and methods using nerve cuffs. Nerve cuff electrodes are provided which can include a tubular body having a longitudinal slit and a flap curled over the slit. The tubular body interior can have a central cathode formed of two opposed and electrically coupled plates disposed between two anodes each formed of two opposed and electrically coupled plates. The tube interior region opposite the slit can be free of electrode material, such that the flexibility of the polymeric tube significantly determines the flexibility and strength of tube opening and closing. Some cuffs include a hinge region having a non-linear effective spring constant which can be higher at low cuff openings and lower at large opening to provide an effective yet non-damaging closing force over a wide range of cuff openings. In use, the tube body can be pulled apart using attached suture loops, with one loop and flap pulled under the nerve followed by part of the tubular body. The tubular body can be closed over the nerve and the flap closed over the tube slit. The nerve cuff can be placed minimally invasively over the nerve and used for neuromodulation and/or sensing purposes.

16 Claims, 22 Drawing Sheets

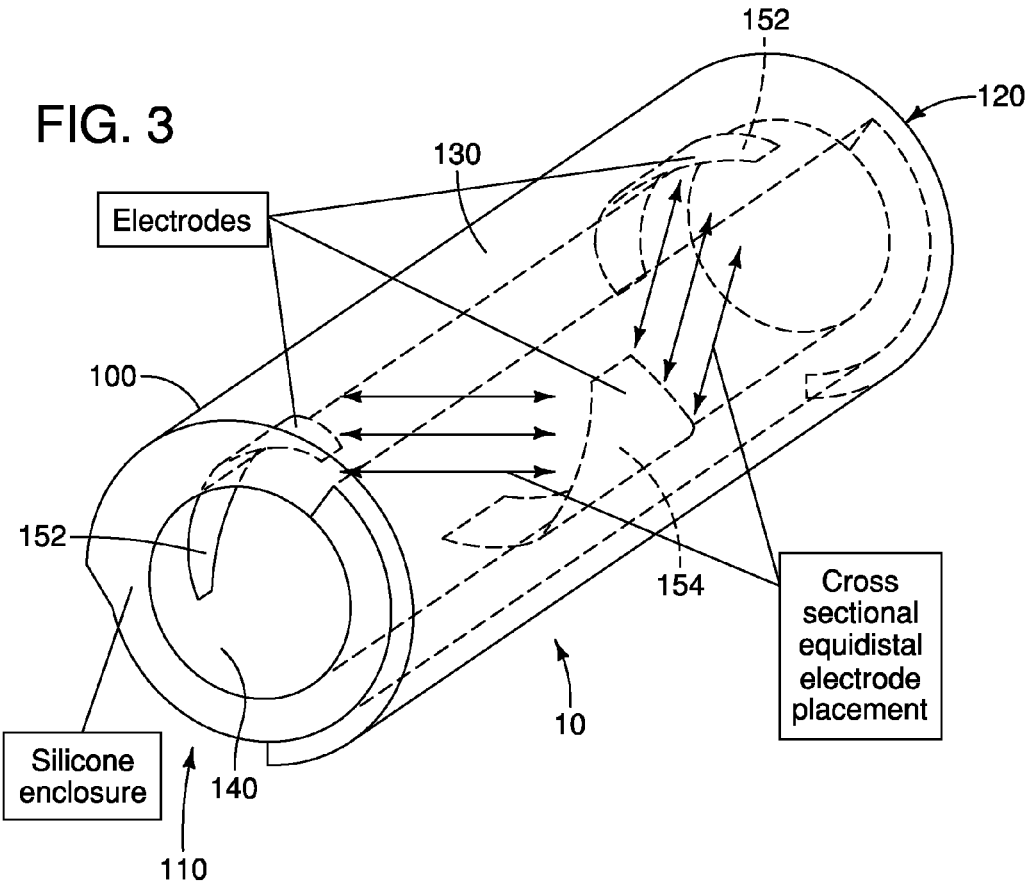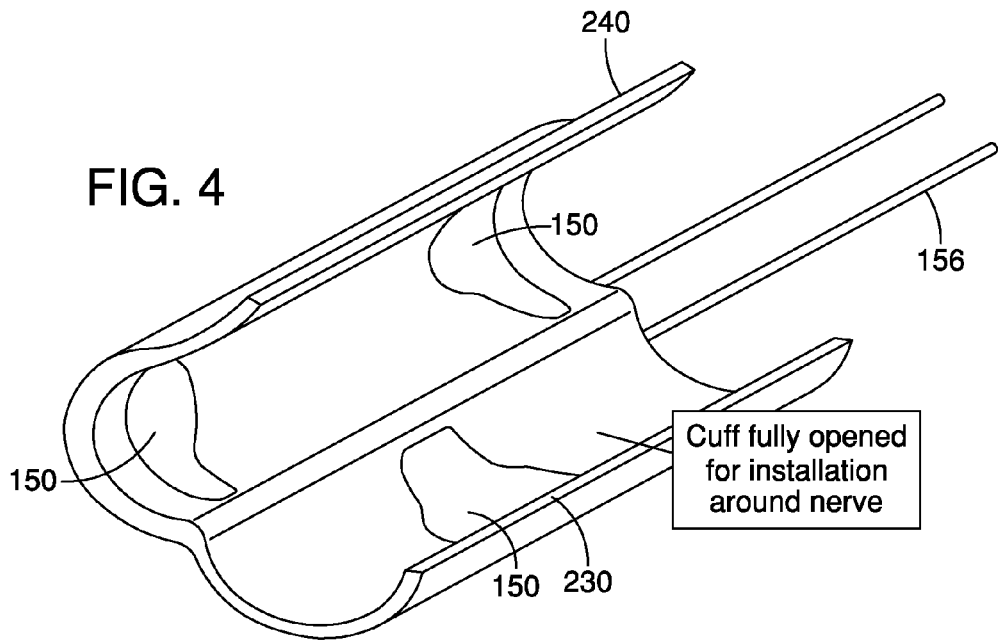

(a) surface mounted electrode (b) simple recessed electrode (c) exponentially recessed electrode (d) conically recessed electrode (e) stepwise sampling of a conically recessed electrode

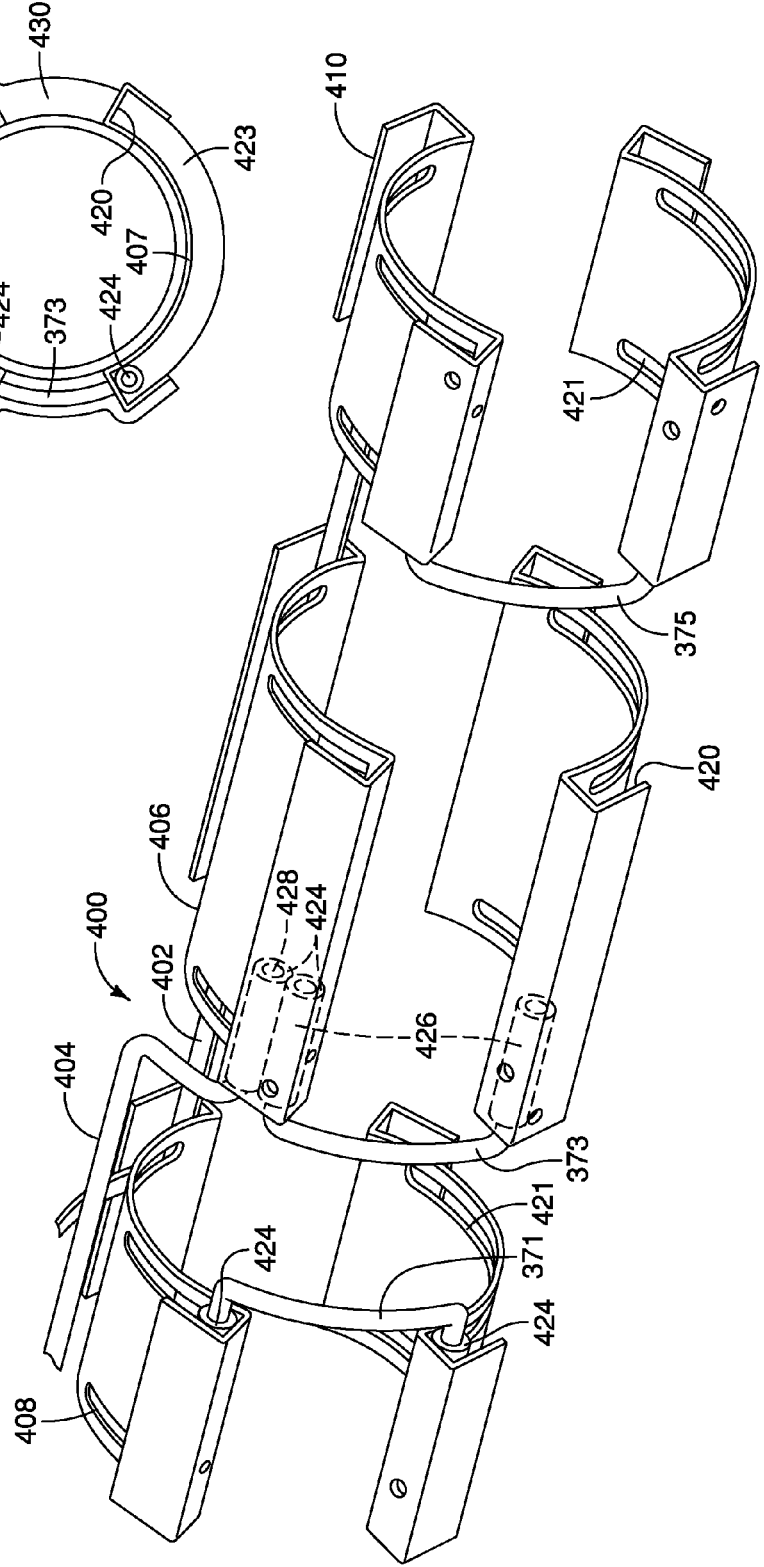

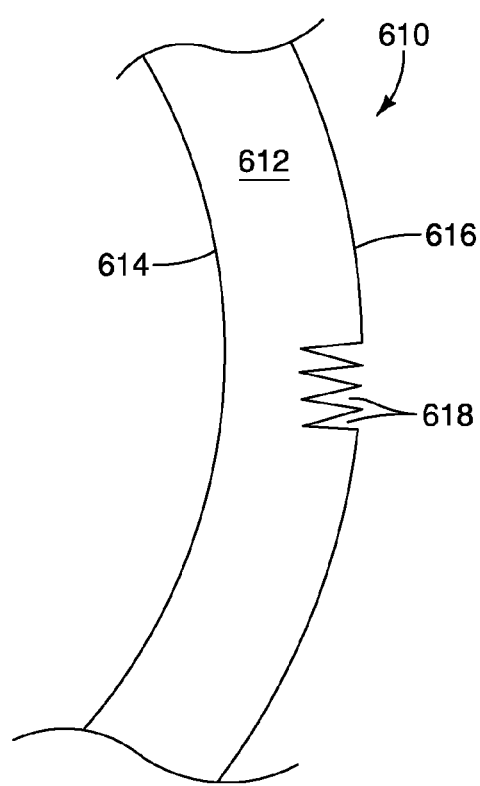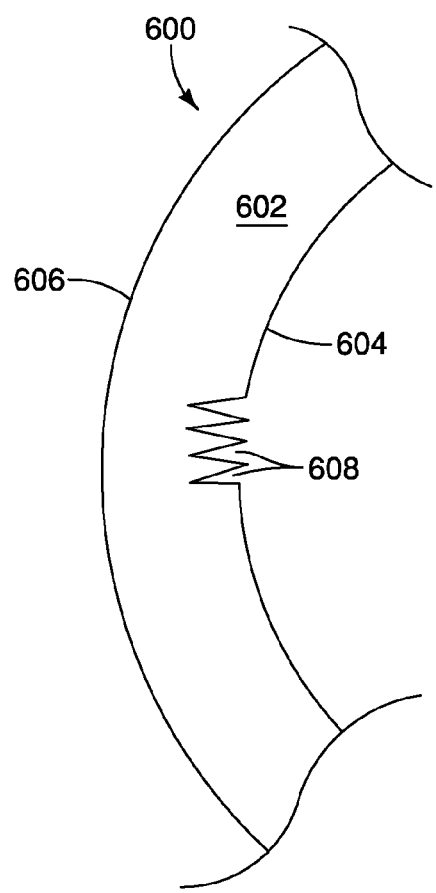

CUFF ELECTRODE HAVING TUBULAR BODY WITH CONTROLLED CLOSING FORCE

RELATED APPLICATIONS

The present application: is a non-provisional of U.S. Provisional Patent Application No. 61/036,429 titled CUFF ELECTRODE HAVING TUBULAR BODY AND SPLIT ELECTRODES filed Mar. 13, 2008; and is a non-provisional of U.S. Provisional Patent Application No. 60/952,219 titled SELF-SIZING NERVE CUFF ELECTRODE filed Jul. 26, 2007.

TECHNICAL FIELD

The present application is related to medical nerve electrodes. More specifically, the present invention is related to nerve cuff electrodes which find use in both nerve stimulation and sensing.

BACKGROUND

The nervous system comprises billions of neurons, organized into structural and functional assemblages, that perform a wide range of functions For example, some neurons relay information from the central nervous system (CNS) to other parts of the body, while others collect information from peripheral sensors either for use by reflexive systems or for interpretation by the CNS.

One type of organized structure of the nervous system is that of nerves. Nerves are bundles of axons, and may include additional support cells, such as glial cells. A single nerve can contain thousands to upwards of a million individual axons, each axon being a specialized structural modification of a neuronal cell. The body comprises a number of nerves, each one typically serving particular functions or relaying particular types of information to and from particular parts of the body. In general, the relay of information through the nervous system is carried out by the activity of excitable cells such as neurons. Neurons are characterized by the ability to respond to stimuli, to conduct impulses, and to communicate with each other or with other types of responsive cells.

In neurons, this ability arises due to structural and biochemical specializations, the most important of which is the ability to maintain an electrical potential across the cellular membrane of the neuron. This membrane potential is due to the action of integral membrane ion "pumps" that produce and maintain an asymmetric distribution of sodium and potassium ions across the membrane, in which 3 sodium ions are pumped out of the cell in exchange for 2 potassium ions pumped inwards. The net effect in a typical neuron is that the electric potential difference across the membrane is typically in the range of −70 mV, referred to as a resting potential.

In addition to mechanisms that produce the asymmetric distribution of sodium and potassium ions that create the resting potential, excitable cells like neurons also have structural and biochemical mechanisms that result in depolarization of the cell membrane, resulting in a wave of electrical activity that propagates along the surface of the neuron.

Depolarization can be caused either by chemical or direct electrical stimulation of the cell. Typically depolarization occurs initially as a localized event on the neuron cell surface that results in the opening of voltage-gated sodium channels. Opening of these channels allows sodium to diffuse into the cell driven along its electrochemical gradient. This results in a reduction in the potential difference across the membrane, which in turn opens more voltage-gated sodium channels, allowing more sodium into the cell, which further depolarizes the cell. Once a threshold level is reached, the cells will completely depolarize, leading to the production of an action potential.

Once initiated, an action potential will be propagated down the length of the neuron, for example, down the axonal portion of the cell. The speed of conduction is dependent on the diameter of the axon, as well as other factors, such as whether the nerve is myelinated or non-myelinated. Larger diameter neurons generally conduct action potentials more rapidly, as do fibers that are myelinated. Stimulation of neuronal signaling can occur naturally in a number of ways. For example, some neurons have cell surface receptors that bind to specific signaling molecules. In response to ligand binding, the receptors in turn signal ion channels to open or close, which can lead to depolarization or hyperpolarization of the neuron. Hyperpolarization leads to de-sensitization of the nerve, while depolarization sensitizes the nerve and increases the likelihood that a stimulus will result in the production of an action potential.

Neurons can be artificially stimulated to depolarize by application of an electrical signal. In these cases, the electrical signal directly acts on voltage-gated channels in the cell membrane leading to depolarization. If a signal of sufficient intensity is applied, an action potential can be evoked.

In addition to the production of an electrical signal, neurons in particular are also able to provide information coding, depending on the frequency at which depolarization occurs, the timing of depolarization or even simply on whether the neuron is firing or not.

Cuff electrodes are well known in the neurostimulation field. Cuff electrodes can be used to stimulate and/or measure the response of peripheral nerves. A cuff electrode can wrap around the nerve to be stimulated and/or sensed.

At least one prior art nerve cuff includes a sheet biased to curl into a tubular spiral when released or wrapped around a nerve. Applicants believe this design is less than optimal for at least two reasons. The first reason is manufacturability. A nerve cuff may have nominal dimensions of 1 cm by 1 cm. One method for biasing the sheet to curl is to stretch a first sheet and adhere the first stretched sheet to a second sheet, allowing them to securely bond. Electrodes would presumably be secured to the first sheet or within recesses in the first sheet. Applicants are unsure as to the reproducibility of such a process with respect to the inwardly directed force on a nerve, among other properties.

A nerve may be teased out of the surrounding tissue, often using blunt dissection tools. This isolation of the nerve may irritate the nerve, which may lead to swelling of the nerve, as would be expected with many other tissues. This swelling can increase the outer diameter of the nerve.

During placement of the nerve cuff, the inwardly directed pressure of the cuff should fall between two extremes, both disadvantageous. If the cuff applies too much pressure on the nerve, the nerve can be damaged. If the cuff applies an initially proper amount of pressure and the nerve swells, then too much pressure may be applied if the cuff does not expand enough.

If the cuff does not apply enough pressure on the nerve, this often means that the cuff is not closely fitted to the nerve, and the cuff can become dislodged from the nerve, particularly during placement. This can allow an undesirable amount of fibrotic tissue ingrowth. This can also force the current applied to the cuff electrode to be larger than optimal, shortening battery life and perhaps even allowing stray currents to effect nearby tissue. If the cuff is initially properly situated, and the nerve later returns to normal size, then the cuff should shrink in order to maintain the proper fit around the nerve.

What would be advantageous is a nerve cuff which can be easily placed using minimally invasive techniques. What would be beneficial is a nerve cuff which is self sizing yet efficient and has a well defined closing force.

SUMMARY

It is of interest to specifically stimulate individual nerves in order to selectively probe physiological functions, or to produce desired physiological effects, or to mimic selected physiological states. For example, stimulation of the sympathetic nerve, and in particular the splanchnic nerve, can be used to produce neuronal signals that create a sense of satiety.

In some instances, an external signal generator, or an implantable pulse generator (IPG), generates an electrical impulse that is transmitted to the nerve through an electrode placed, near, or in direct contact with the nerve surface. While this approach generally results in neural stimulation, the design of the electrodes result in limitations in the effectiveness and specificity of stimulation.

For example, in using electrodes to simulate nerves, it is desirable to secure the electrodes to the nerve in some fashion, in order to maintain a consistent electrical pathway between the electrode and the nerve to be stimulated. This is especially important where the electrode is designed for long-term use, for example in providing electrical stimulation to a nerve as part of a medical therapeutic regime, or where a specific region in the body, or portion of a nerve is to be stimulated. One approach is preparing various types of electrodes that can be wrapped around a portion of the nerve to be stimulated, so-called cuff electrodes. By wrapping the electrode around the nerve, movement of the electrode is limited, and contact between the nerve and electrode is potentially improved. A number of different cuff electrode configurations exist in the prior art, including rigid cuffs, flexible cuffs, and helical electrodes.

Some embodiments described herein provide a self-sizing cuff electrode that maintains a relatively even contact pressure between the electrically conducting surfaces of the electrode and the nerve. In addition, and as disclosed herein, some embodiments of the present electrodes can be effective to provide an electrical pathway between the conducting surfaces (for example, an anode and cathode) that results in current flow cross-sectionally through the nerve, as opposed to along the surface, as in some electrode designs.

Some embodiments of the present invention provide a cuff electrode which can be used to stimulate a wider range of nerve sizes, when compared to many other cuff electrodes. The present invention cuff electrodes can provide an efficient electrode which allows for long term use with an implanted battery. The design of such cuffs can provide resistance to fibrotic ingrowth.

The improved design of some embodiments of the present invention provide both a large electrode surface area encircling much of the nerve while providing a flexible cuff which can gently adjust to the nerve size, as the nerve changes size to a post operative inflamed state and back to a smaller diameter state.

The present invention includes self-sizing cuff electrodes for use in stimulating a nerve, the cuff electrode including a cuff portion configured to adopt a generally tubular shape, the cuff portion being configured to contact a nerve over a contact area. The cuff portion can also include a hinge portion configured to provide resilient support along substantially the length of the cuff portion. The cuff portion can include a longitudinal split, forming a first edge and second edge configured to slidably overlap each other such that the cuff portion substantially circumferentially encloses at least a portion of the nerve. The cuff may also include a plurality of electrodes including at least one anode and at least one cathode, located on substantially opposite sides of the nerve when the nerve is enclosed by the cuff portion. In response to an electrical signal, the anode and cathode can form an electrically coupled anode-cathode pair with an electrical pathway therebetween, wherein the cuff portion is configured to provide a compressive force effective to maintain contact between the electrodes and the nerve, such that the electrical pathway between the electrodes and the nerve is maintained.

In some cuffs the compressive force is maintained in a range of about 10 mm to about 30 mm Hg, and in others the compressive force is maintained in a range of about 2 mm to about 30 mm Hg. Some cuffs have a hinge portion including at least one elastic member. The hinge portion is configured to yield before the force of the cuff on the nerve exceeds about 20, 25, or 30 mm Hg, in various embodiments.

Some cuff electrodes according to the present invention include a first elongate conductor, a second elongate conductor, a first pair of opposed curved electrically conductive plates electrically coupled to each other and to the first conductor, a second pair of opposed curved electrically conductive plates electrically coupled to each other and to the second conductor, and a third pair of opposed curved electrically conductive plates electrically coupled to each other and to the first conductor. The first, second, and third pairs of curved electrically conductive plates each can have an electrically exposed interior surface. The cuff electrode can also have an elongate flexible shaft having a proximal region and can be operably coupled to the shaft distal region, with the cuff including a tubular body having an interior region and an exterior region. The first, second, and third curved electrically conductive plates may be operably coupled to the cuff tubular body interior region such that the electrically conductive plate interior conductive surface is electrically exposed within the cuff tubular body interior. The cuff tubular body can include a tubular body wall having a longitudinal slit therethrough allowing the cuff tubular body to open to expose the cuff tubular body interior, and in which the cuff tubular body is biased to urge the tubular body to close the slit.

In some such embodiments, the opposed curved electrically conductive plates are electrically coupled to each other through electrically conductive wires, where the wires may be biased to urge the opposed plates closer together. Some cuffs further a flap secured to the tubular body on a first side of the slit, in which the flap wraps around the tubular body and covers the slit, and in which the flap tapers to a free end of the flap. Some tapered regions include at least one removable flexible member which is adapted to being grasped to pull the tapered flap region under a nerve. The removable flexible member may include a loop of suture material secured to the flap tapered region.

In some such embodiments the opposed plates have longitudinal edges near the slit and opposite the slit, where the edges near the slit and opposite the slit are disposed about the same distance from the opposing plate respective longitudinal edge when the slit is closed. The opposed plates can have longitudinal edges near the slit and opposite the slit, where the edges near the slit are disposed a greater distance from the opposing plate respective edges than the edges opposite the slit, when the slit is closed. In other embodiments, the edges near the slit are disposed a lesser distance from the opposing plate respective edges than the edges opposite the slit, when the slit is closed. The cuff tubular region between the opposed plates and opposite the slit is substantially free of electrode material in some embodiments.

Some cuffs can open to varying degrees to receive a nerve, and the cuff tubular region between the opposed plates and opposite the slit form a hinge region having a non-linear spring constant, wherein the spring constant is substantially greater at small degrees of opening degree than at large degrees of opening. Some cuffs have at least about 2 mm Hg closing force at 5 degrees of opening and no greater than about 30 mm Hg at 90 degrees of opening. Some cuffs have a hinge region which includes a first element providing cuff closing force, where the first element substantially decreases in closing force past a first degree of opening limit. The hinge region may also include a second element providing closing force, where the second element continues to provide cuff closing force past the first cuff opening limit. Some cuff have a hinge region which includes a weakened region susceptible to folding a large degrees of opening, the hinge region further having an inner wall disposed between the hinge weakened region and an outer wall disposed away from the weakened area and inner wall, such that the first element includes the hinge region outer wall.

Some embodiments include jumper wires coupling the opposed plates and are biased to close the cuff tubular body. The jumper wires can be biased to close the cuff tubular body in a non-linear fashion, such that the jumper wires have a spring constant which decreases with increasing cuff tubular body opening.

Some cuff embodiments have a spring force provided at least in part by a longitudinal channel in a tubular cuff wall region substantially opposite the cuff opening, in which the tubular wall region includes an inside wall and an outside wall, such that the inside wall provides a tension closing force and the outside wall provided a compressive closing force, where the outside wall buckles under a compressive force at an opening limit and wherein the inner wall tension force continues with further cuff opening after buckling.

In some embodiments, a compressible element is disposed within the hinge region lumen, such that buckling of the hinge region outer wall allows the hinge region lumen to decrease in at least one dimension, which can allow the hinge region lumen walls to bring radial, compressive forces to bear on a compressible member disposed within. In some embodiments, the compressible member includes a shaft. In other embodiments the compressible member includes a tube having a tube lumen within. When the tube lumen walls have been sufficiently compressed and forced inward, then the inner member can itself compress and/or buckle, depending on the embodiment. In various embodiments elastomeric foam shafts and/or tubes are used, as are resilient elastomeric member tubes. Spring members may be included within the hinge region lumen in some embodiments. Some embodiments have a gap between the inner member and the hinge region lumen inner wall. In this way the hinge region wall can buckle and force the hinge region lumen wall to close in on the inner member and to apply a compressive force on the inner member. In still other embodiments, at least the cuff hinge region is co-extruded, allowing different materials to be used for the inner vs. outer wall in the hinge region. Some embodiments include a thicker outer wall then inner wall in the hinge region. This can provide a larger initial closing force with initial cuff opening.

The present invention also includes methods for disposing a nerve cuff about a nerve, one such method including advancing a nerve cuff selected from any of the embodiments disclosed herein, toward the nerve, at least partially freeing the nerve from nearby tissue, advancing the cuff flap under the nerve, allowing the cuff tubular body to close over the nerve, and allowing the cuff flap to wrap around the tubular body to cover the tubular body slit. Some methods further include pulling the cuff flap under the nerve using a flexible graspable material. Methods may also include pulling the cuff tubular body open about the slit by pulling on graspable flexible members secured to the cuff on either side of the slit. Some embodiment methods further include pulling the cuff tubular body open about the slit by pulling on a first graspable flexible member secured to the cuff tubular body near one side of the slit and pulling on a second graspable flexible member secured to the cuff flap which is secured to the cuff tubular body on an opposite side of the slit from the first graspable member. In some of these methods, the cuff is advanced minimally invasively, through a hole less than ½ inch in maximum extent.

DESCRIPTION OF THE DRAWINGS

FIG. 3 illustrates a perspective view of one embodiment of a self-sizing cuff style electrode showing one possible placement of electrodes.

FIG. 4 illustrates a view of one embodiment of a self-sizing cuff electrode in an open configuration prior to placement around a nerve.

FIG. 22 is a fragmentary, perspective view of the curved electrode plates and jumper wires of FIG. 21.

FIG. 23 is an end view of the subassembly of FIG. 22, showing the conductor wires at the top and one jumper wire at the left side.

FIGS. 25A and 25B are fragmentary, cross sectional views of tubular cuff electrodes having material sections removed in the tube cuff wall opposite the tube slit.

DETAILED DESCRIPTION

Neural stimulation can be accomplished by directly applying an electrical charge via an electrode (or electrodes) to a surface of a nerve. In general, electrodes comprise a holder of some type into which electrically conductive materials are placed, as well as points of contact on which to attach lead wires that connect the electrodes to the signal generator or IPG. In addition, where the electrode is designed for long-term use, for example when used in an implantable system for medical or research use, there must also be some way in which to keep the electrode in position and in contact with the nerve of interest.

Figure 1:
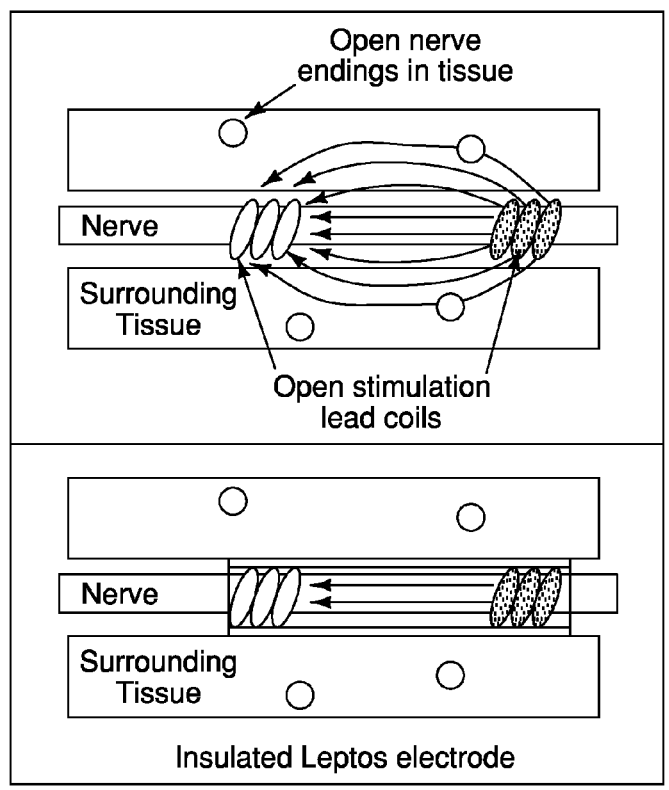
FIG. 1 is a diagram comparing the effects of nerve stimulation using an unenclosed electrode and an enclosed electrode.

FIG. 1 illustrates a simple case, in which the electrodes can be bare material laid on or around a nerve. For example, the open stimulation lead coils shown in FIG. 1 (upper panel), can be used to stimulate a nerve. A serious drawback of an open lead system, however, is that current is free to flow into surrounding tissue, and not all current is directed to the nerve to be stimulated. The surrounding tissue in FIG. 1 includes some open nerve endings in the tissue, represented as circles drawn in the tissue.

In an open lead system, stimulating current can produce stimulation of nerve fibers in the surrounding tissue. Depending on the type of fibers, inadvertent stimulation may be perceived, for example by a patient, and may lead to discomfort, or the inappropriate activation of other neuronally regulated systems. This can lead to reduced selectivity or specificity with respect to the neural system that one is attempting to regulate with the IPG system. To compensate, it may be necessary to reduce the stimulation intensity in order to avoid stimulating unwanted nerve fibers. This in turn may reduce the effectiveness of stimulation of the nerve that is intended to be stimulated.

In some embodiments, electrodes may be electrically insulated by means of an external shield in order to prevent current leakage outside the area of interest. As shown in FIG. 1 (lower panel), this results in more effective energy delivery to the nerve of interest and increased selectivity and specificity of the stimulation regime. In addition, as shielding results in a greater proportion of the total energy being delivered to the desired nerve, less overall input energy is needed for effective stimulation. Where the device is an IPG, this will tend to improve the service life of the device due to lower overall energy consumption from the IPG power source (e.g., an implanted battery) over time.

Figure 2:
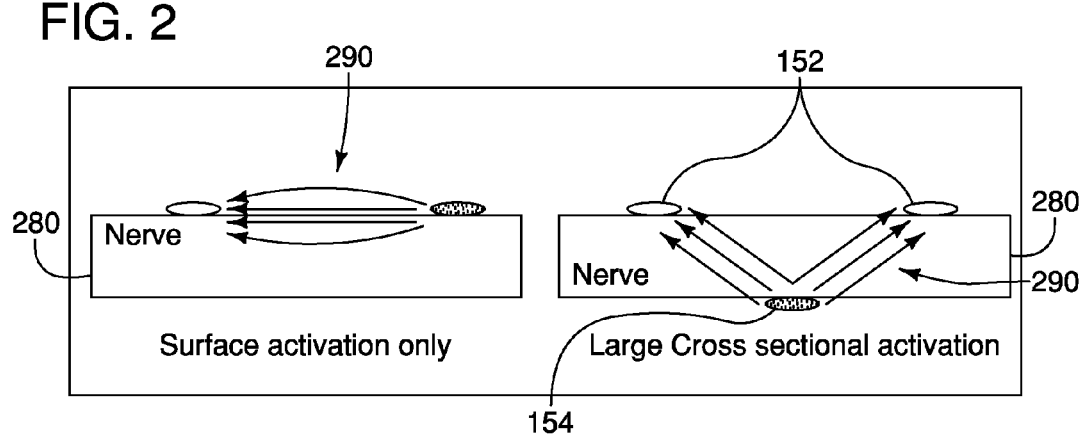
FIG. 2 depicts the difference between surface and cross-sectional activation of a nerve.

FIGS. 2-4 illustrate embodiments of a self-sizing cuff electrode assembly 10. In some embodiments, the shielding function is provided by the enclosing member, or cuff 100 portion of the assembly. The assembly further comprises electrodes 150, which in some embodiments can be anodes 152 or cathodes 154.

Conveniently, in some embodiments the cuff 100 can be made from a material, such as silicone rubber, that is resilient, electrically insulative, and biocompatible. By placing an insulative material between the electrodes 150, which are located on the inner surface 140 of the cuff 100, current flow (indicated at 290) is more likely to flow between the electrodes 152 and 154 and through the nerve 280, as opposed to leaking away from the nerve where it could otherwise result in unwanted stimulation of surrounding tissue and/or other nerve fibers.

A challenge in electrode design is in providing an electrode placement that is effective to stimulate as many neurons within a nerve as possible so that the full effect of stimulating the particular nerve can be realized while minimizing unwanted stimulation of adjacent nerves fibers or excitable tissues (e.g., muscle). As in other types of electrical circuits, the electrical pathway formed when applying electrical energy to a nerve via electrodes will be the path of least resistance. Consequently, the placement of electrodes with respect to each other is important.

Many stimulation devices use an electrode arrangement that results in an electrical pathway oriented along the surface of the nerve, as shown in FIG. 2 (left panel). For example, U.S. Application 200610030919 by Mrva et al., the entirety of which is incorporated by reference herein, discloses a cuff-style electrode in which the electrical contacts are arranged either axially or longitudinally with respect to the nerve bundle. In the Mrva device, the electrodes are situated such that the shortest distance between electrodes (i.e., the pathway for current) is along the surface of the nerve. Similarly, in U.S. Pat. No. 5,282,468 to Klepinski, the entirety of which is incorporated by reference herein, the electrodes are arranged circumferentially, with the result that the electrical pathway will be along the nerve surface. However, the limitation resulting from electrodes that create a surface-oriented electrical pathway is that a significant number of the neurons in the interior of the nerve will not be adequately stimulated. Thus, to fully stimulate the nerve requires increased signal intensity, which in turn leads to several problems already identified and discussed above.

As a result, it may be desirable to configure the device such that the placement of the electrical contacts (i.e., the electrodes) results in an electrical path that is oriented cross-sectionally across the nerve, as opposed to along the nerve surface, as illustrated in FIG. 2 (right panel). In embodiments of the present disclosure, the electrodes are arranged such that the electrical path for the stimulation current is oriented to pass cross-sectionally, rather than along the nerve surface as in prior art devices. Thus, in embodiments presently disclosed, the electrodes are effectively horizontally opposed, such that each anode-cathode "pair" is situated on substantially opposite sides of the nerve to be stimulated. In this arrangement, the electrical pathway between an anode-cathode pair may be cross-sectionally across the nerve, while less desirable surface stimulation will be reduced or non-existent.

For example, in one embodiment, as shown in FIG. 3, the electrode cuff comprises a silicone enclosure that further comprises three electrodes. In the illustrated embodiment, the cuff includes a centrally located cathode, and two anodes located towards each end of the cuff. This arrangement results in each anode between equidistant from the cathode and placed in such a way that the stimulation current will flow across the nerve as opposed to along the surface of the nerve, as is the case with prior art cuff electrodes.

While the embodiment illustrated in FIG. 3 depicts one cathode and two anodes, other electrode arrangements are possible that will fall within the scope of the disclosure as presented herein. For example, it is possible to provide a cuff with a centrally located anode, and two distally located cathodes, and still retain an equidistant relationship between anodes and cathodes, with the result that the current path will flow cross-sectionally through the nerve.

In some embodiments, a plurality of anodes and cathodes can be provided and arranged such that the equidistant, cross-sectional arrangement is preserved between a plurality of anode-cathode pairs. As used herein the term "anode-cathode pair" is intended to have its plain and ordinary meaning, which includes, without limitation, an anode and cathode that are configured to be electrically coupled such that current passes between them and through the nerve when a current is applied by a signal generator or IPG to the electrodes.

Thus, the present disclosure is not limited to neural stimulation devices with particular numbers of anodes or cathodes, and all such devices are intended to fall within the scope of the present disclosure. It should also be understood that the term "equidistant" as used herein does not mean exactly the same distance, but rather the various anode-cathode distance in the assembly are substantially the same. The distribution of stimulation current in the nerve is to a great extent determined by the electrical resistance of the current pathway between respective anodes and cathodes. If the distance between anodes and cathodes varies, a higher current density will be observed at the region where the anode is closest to the cathode. As a result, stimulation of nerve fibers between the anode and cathode will be more variable, and in some cases, significant numbers of fibers may be less adequately stimulated, leading either to a loss or reduction of the desired physiological response. In contrast, by shaping the anodes and cathodes, such that an equal distance is maintained over a greater area, more effective stimulation of a greater number of neurons within the nerve will occur. Such a pattern of current flow is not possible with prior art devices.

As shown in FIGS. 3 and 4, the electrodes can comprise shapes other than simple strips of material. In addition, the respective shapes of anodes and cathodes can be configured to optimize the equidistant relationship between anodes and cathodes. This can increase the "width" of the electrical pathway, while still maintaining a relatively equidistant relationship between anodes and cathodes. Thus, shaping the electrodes can provide additional advantages.

Providing a plurality of anodes and cathodes, for example the tri-polar arrangement depicted in the illustrated embodiments of FIGS. 3 and 4, also provides useful advantages. For example, a centrally located cathode will distribute current across a greater section of the nerve, thus activating a greater volume than would result from a conventional bi-polar design. In addition, providing multiple electrodes allows for more complex stimulation patterns.

For example, in a device such as that illustrated in FIG. 3, it is possible to vary the stimulation pattern and intensity to the anodes independently. This enables one to recruit different afferent and efferent fibers within the same nerve using a single electrode assembly. In such a case, the IPG or other signal generator would comprise circuitry such that each anode (or cathode, if multiple cathodes were used) would be controlled by an independent channel, such that a number of independently controlled electrical simulation pathways could be produced in the nerve. Alternatively, the electrodes could be electrically linked, such that a stimulation pattern could be effectively applied over a greater area of the nerve. In some embodiments, the circuitry could be configured to change between linked and independent modes of stimulation to provide the greatest number of stimulation options. The supporting structure for the electrodes comprises a cuff 100 configured to spontaneously form a generally tubular structure. The self-curling feature of the cuff is a property that can be provided by the material used to fashion the cuff, as well as the shape of the cuff. For example, the cuff can be molded as a split tube using a compliant material such as silicone rubber or a biocompatible compliant polymer.

Figure 5:
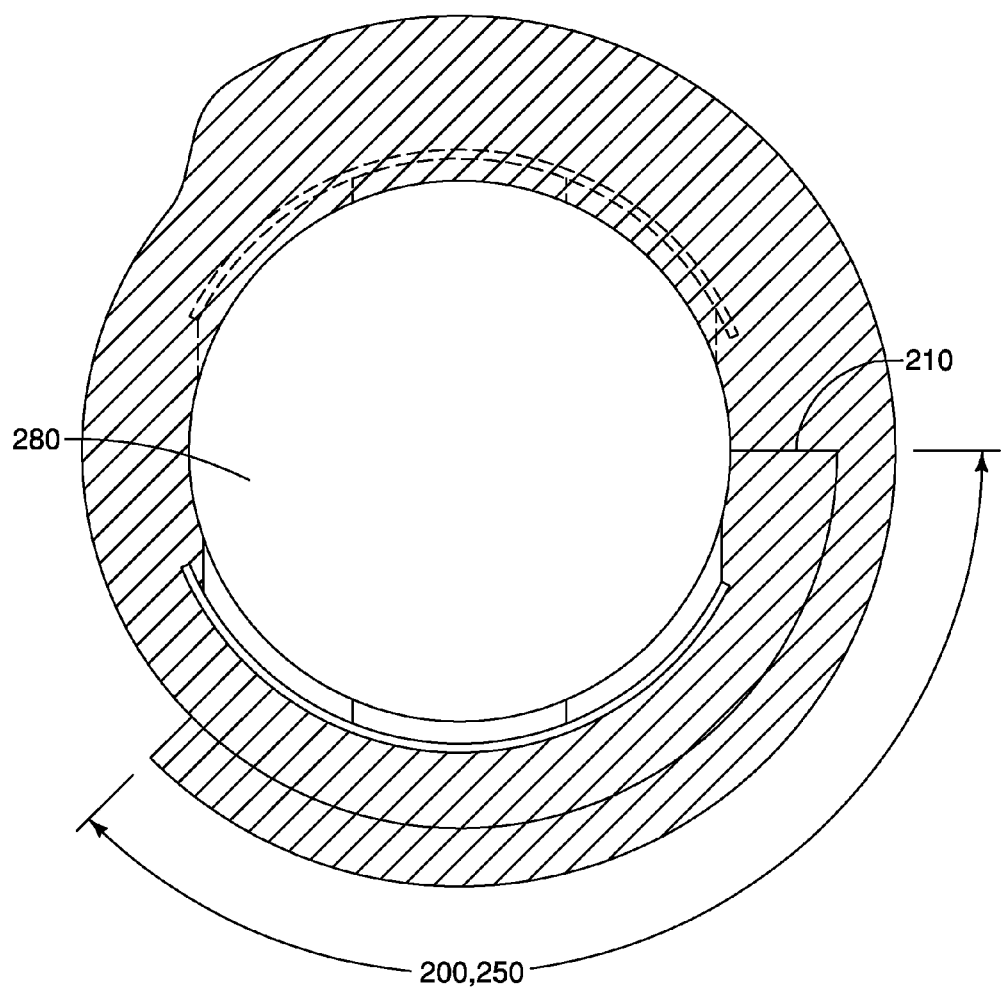
FIG. 5 is a cross-sectional end view of one embodiment of a self-sizing cuff electrode showing the overlap region.

Thus, the cuff can be manufactured in the shape it will assume when placed around the nerve. Conveniently, the use of a compliant material and providing a longitudinal split region 250, permits the cuff 100 to be laid open for placing under a nerve, using surgical forceps or other suitable instruments capable of grasping the first and second edges, as illustrated in FIG. 4. To complete the placement of the cuff 100, the edges would be released in a controlled manner, such that the first and second edges would overlap, as in FIG. 5, and the cuff would assume its original tubular shape, thus enclosing the nerve and placing the electrodes 150 in contact with the surface of the nerve.

In some embodiments, as shown in FIG. 3, the cuff 100 comprises a sheet of an elastomeric material, for example silicone rubber, that is electrically insulative, compliant, and biocompatible. The cuff 100 comprises a first end 110 and a second end 120, an outer surface 130, and an inner surface 140. Electrodes 150 are located either on, or embedded into the inner surface 140 of the cuff 100. The cuff 100 is configured to perform a number of functions. First, the cuff provides a structure onto, or into, which the electrodes 150 can be situated. In some embodiments, the electrodes 150 are placed on the inner surface 140 of the cuff 100. In these embodiments the electrodes 150 can be secured with biocompatible adhesives, or with other forms of securement well known in the art. In some embodiments, for example those shown in FIG. 6, the electrodes can be located within a recess 220 in the inner surface 140 of the cuff 100. Recessed electrode surfaces provide an advantage in that they facilitate better cross-sectional current distribution across a nerve as well as more uniform charge injection into the tissue (e.g., a nerve) being stimulated (FIG. 6; Suesserman et al., IEEE Trans. Biomed. Eng. 38: 401-408, 1991, the entirety of which is incorporated herein by reference).

The cuff 100 comprises an enclosing member that is configured to spontaneously adopt a generally tubular shape that encloses the nerve 280, and in turn places the electrodes 150 in contact with the surface of the nerve 280. The cuff is preferably made from a resilient material such as silicone rubber, although other materials known to those of skill in the art will perform the necessary functions of the cuff 100. As shown in FIG. 4, the cuff 100 is in effect a sheet of material that is shaped such that it will form the tubular structure shown in FIG. 3. The cuff 100 is thus easy to install at the desired site along a nerve, and once in place, it is allowed to roll up and form a tube with the nerve situated inside the cuff.

In addition, the cuff 100 is inherently self-sizing, such that it will accommodate range of nerve sizes, while maintaining the integrity of the nerve/electrode interface. Moreover, the cuff can be designed that it will maintain a contact pressure within a range of about 10 mm Hg to about 30 mm Hg, over at least a two-fold range of internal diameters, in some embodiments. Significantly, the self-sizing feature also addresses a problem of many cuff style electrode assemblies. It is important in some electrode devices to have an intimate contact between the electrode(s) and the nerve, to ensure that stimulation energy is efficiently delivered. However, the need for "firm" contact must be balanced against the physiological realities of a living tissue such as a nerve. Thus, it is desirable that an electrode device does not impose excessive pressure on the nerve in order to maintain contact, as pressure can, and does, interrupt blood and nutrient supply, which in turn can lead to nerve atrophy.

Therefore, the pressure exerted on the nerve by the cuff can be maintained within a range of pressure which allow on one hand for consistent electrical contact between the electrodes and the nerve, while avoiding physically damaging the nerve. In embodiments of the present disclosure, the cuff is configured such that when it encloses the nerve, a relatively even pressure is maintained over substantially the entire contact area between the cuff 100 and nerve 300. In some embodiments, the pressure is maintained with a range from about 2 mm Hg to about 30 mm Hg.

This is achieved in part by the composition of the cuff material, but as well is provided by additional features of the cuff design. Embodiments of the cuff of the present disclosure include a first edge 230 and second edge 240 that are configured to overlap with each other at 250, when the cuff 100 assumes its tubular conformation, as shown in FIGS. 3-5, 7, and 8. When viewed end on, as in FIG. 5, the overlap of the first edge 230 and second edge 240 that slidably engage each other along a longitudinal split region 250. In some embodiments the cuff 100 comprises a notch 210 into which the first edge 230 can nest. The point at which the first edge abuts the notch 210 can define the smallest effective interior radius of a cuff.

Figure 9:
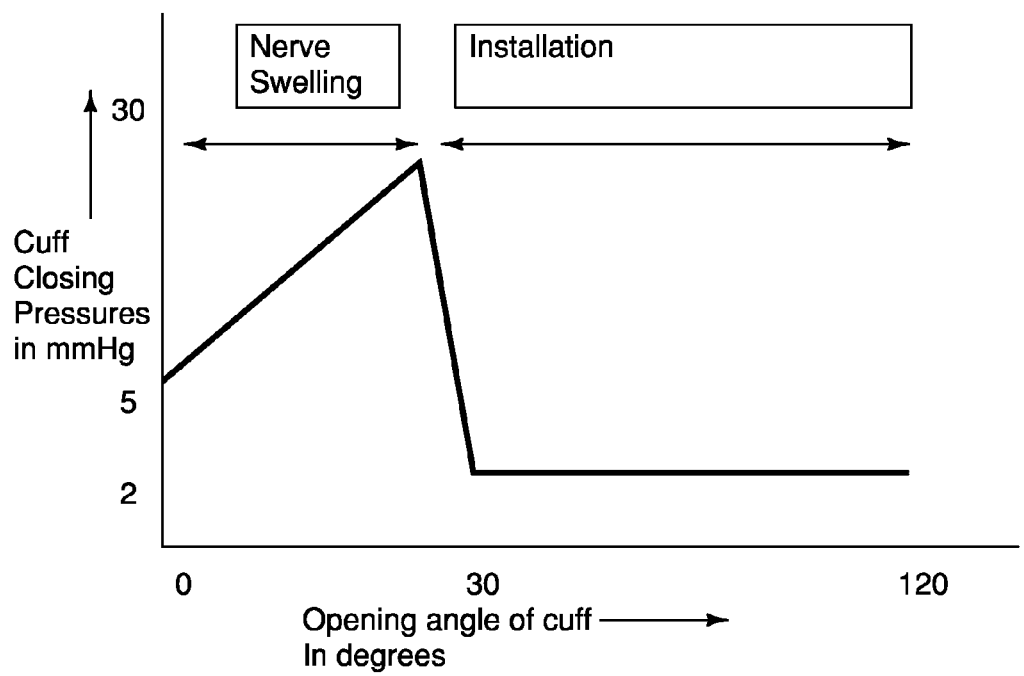
FIG. 9 depicts cuff closing pressures as a function of cuff opening.
Figure 13A:
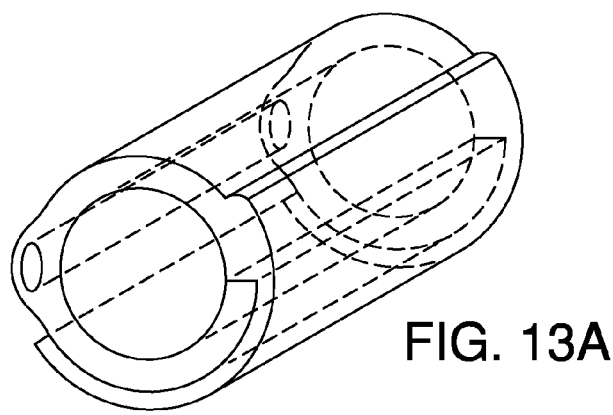
FIGS. 13A-D depict embodiments of a cuff with a hinge area comprising a longitudinal passage and load bearing portion.
Figure 13B:
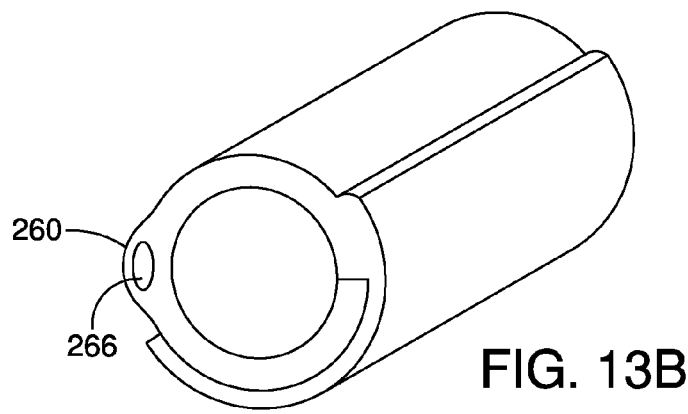
Figure 13C:
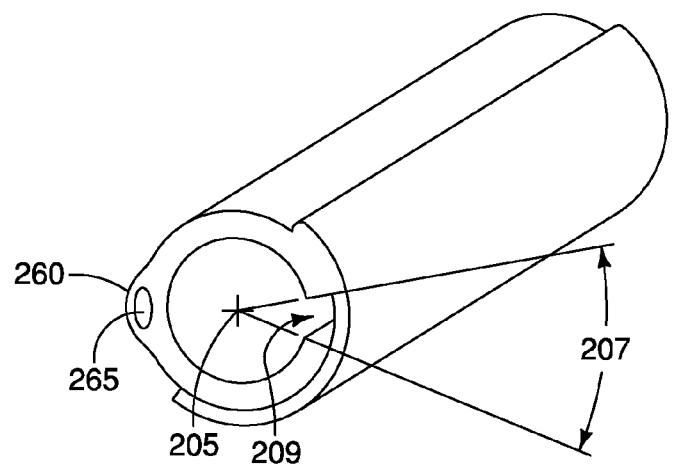
Figure 13D:
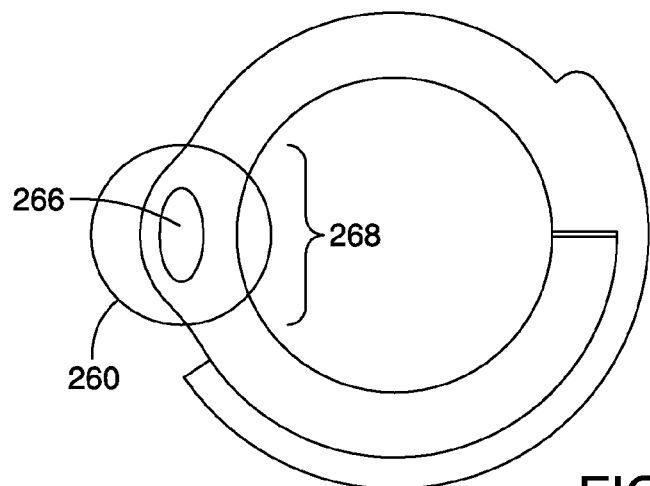
Figure 14A:
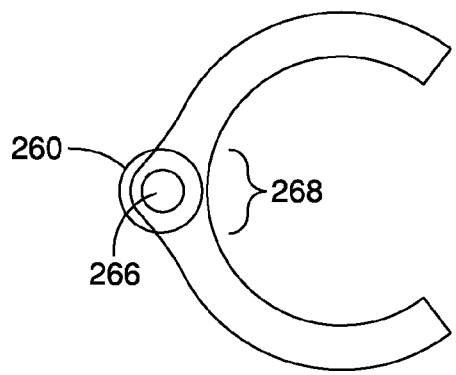
FIGS. 14A-B depicts a cuff like that of FIG. 13 at various opening angles, showing compression and buckling of the hinge passage wall as the cuff is laid open.
Figure 14B:
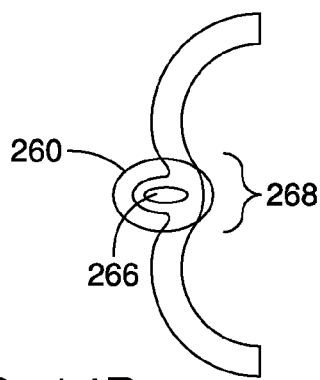

FIGS. 13A-C show that, with respect to the cuff center longitudinal axis 205, the first edge 230 and notch 210 form an angle, or as defined herein, an opening angle 207. In the embodiment shown in FIG. 5, where the first edge 230 and notch 210 are in contact, the opening angle will be about 0°. As the cuff is expanded, the first edge 230 and second edge 240 will slide relative to each other, and a space 209 will form between the first edge 230 and the notch 210. In the expanded state, the first edge 230 and notch 210 will now define an angle relative to the cuff axis 205 that is greater than zero, as shown in FIG. 9. When the cuff is laid open, the opening angle will be about 180°, and the first edge 230 and second edge 240 will not contact each other, as shown in FIGS. 4 and 14B. When the cuff is installed, the length of overlap is chosen to provide a wide enough range of opening angles, while maintaining effectively even pressure over the contact area. Another way to view the interaction of the cuff with the object it encloses is that the cuff resists the expansion that results from a change in diameter due to the enclosed object. The degree of resistance is observed as a pressure exerted by the cuff on the object, for example a nerve, and the design of the cuff is such that this resistance will range from about 2 mm to about 30 mm Hg, when the cuff is installed.

Thus, because the cuff is resilient, as the opening angle increases from about 0°, the cuff will exert an increased pressure (i.e., it will increasingly resist) around any object it encloses. The cuff of the present disclosure is thus designed that as the opening angle increases to about 30°, the pressure of the cuff on the nerve will increase no greater than about 30 mm Hg. The cuff is also designed such that at greater opening angles, the cuff yields so that the value of 30 mm Hg is never exceeded. Nerves swell during the post-operative period, and then over a period of weeks, they shrink back to the pre-operative size. In some cases, the degree of swelling can be as much as 30% of the original diameter. Embodiments of the cuff electrode as disclosed are capable of maintaining a contact pressure between about 2 mm Hg and about 30 mm Hg upon initial placement of the cuff, and during the period of postoperative swelling, and resolution of the post-operative swelling of the nerve, over the range of size changes that are seen in vivo. The length of the overlap region is selected to permit this degree of diameter change, while maintaining effective contact between the electrode(s) and the nerve, and at same avoiding over-compression of the nerve.

Thus, in order to effectively maintain electrical conductivity between the electrodes and the nerve, while avoiding over-compressing the nerve, the cuff must be both resilient (to maintain pressure) and compliant (to avoid over-compression). At the same time, to permit relatively easy installation of the cuff around a nerve, it is an advantage to be able to effectively lay open the cuff (as shown in FIG. 4), so that the cuff can be placed under the nerve at a desired location, for example by sliding the cuff into place, without damaging the resilient components of the cuff that produce the tubular form, and which engage the nerve at the desired pressure (i.e., resistance).

One way in which to accomplish these features would be to include a bias member, such as a spring, that compliantly resists opening of the cuff. However, typical spring behavior is such that as the cuff is opened, the amount of force needed to further open the cuff increases. At extreme opening angles, such as when laying open the cuff for installation, the large opening angle might damage the spring and/or cuff could be damaged. Moreover, the spring member would need to exert relatively low forces, and should not exceed, for example, about 30 mm Hg at any opening angle.

In the present disclosure the resiliency is provided by an elastic hinge 260. The elastic hinge 260 is designed such that it has complex elastic properties. At low opening angles (0° to about 30°), the elastic hinge 260 is operative such that the pressure exerted by the cuff on the enclosed nerve will range from about 2 mm Hg to about 30 m Hg. At higher opening angles, the elastic hinge 260 is configured to yield, due to the action of a release member 265, such that the pressure exerted by the cuff never rises above, for example, about 30 mm Hg. In the embodiment illustrated, release member 265 includes an outer wall alongside the longitudinal lumen 266 in the hinge region. When the angle of opening exceeds a limit, the outside wall can buckle, for example, bulge outward. This failure of the outer wall to provide a force to resist the hinge opening can remove some of the closing pressure on the cuff. When the cuff is closed again, the outer wall preferably resiliently regains its shape to provide closing force on the cuff again. As some nerves can swell to a diameter 30% greater than the pre-operative diameter, the cuff is designed to expand to opening angles in excess of 100° without exceeding the 30 mm Hg pressure limitation. The inner wall of the hinge region can continue to provide an elastic force in tension in some embodiments, even after the outer wall has buckled. This force can be finely selected through the wall thickness and even co-extrusion of a different material than the outer wall, in some embodiments.

Figure 10A:
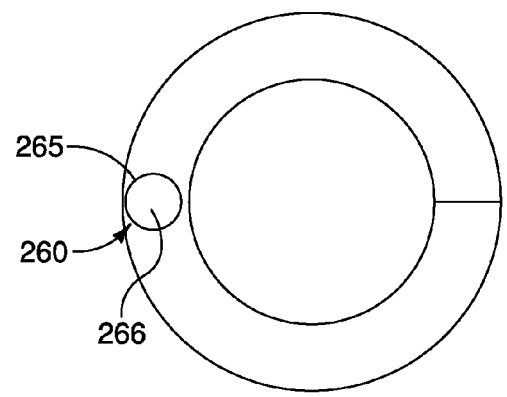
FIG. 10A depicts an end view of a simplified cuff and hinge.
Figure 10B:
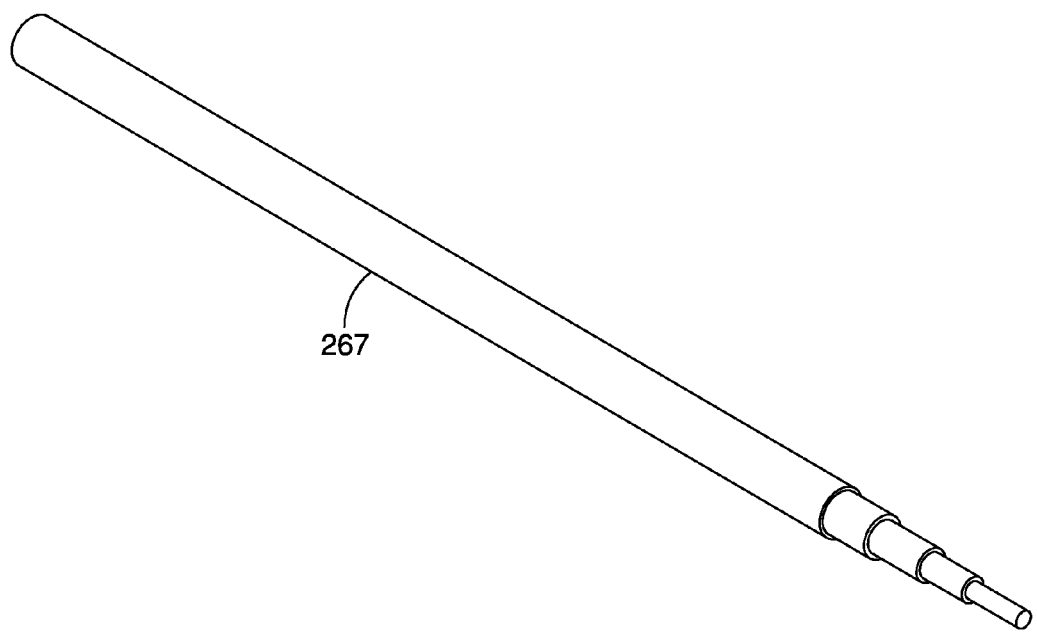
FIG. 10B depicts an exploded view of a multi-element elastic member.
Figure 11A:
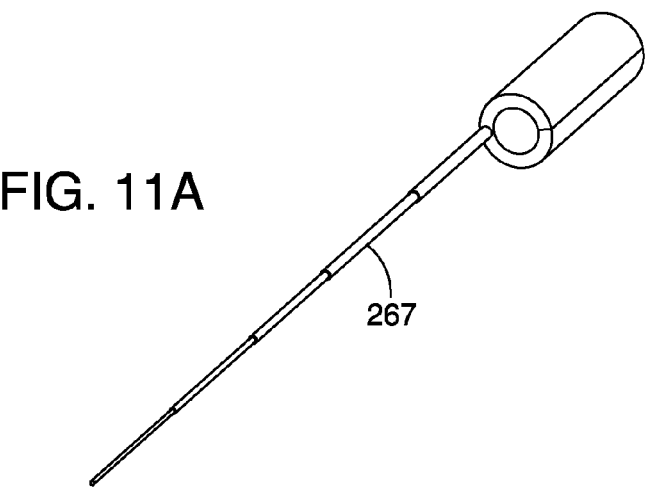
FIG. 11A depicts embodiments of a cuff, and an exploded view of a multi-element elastic member.
Figure 11B:
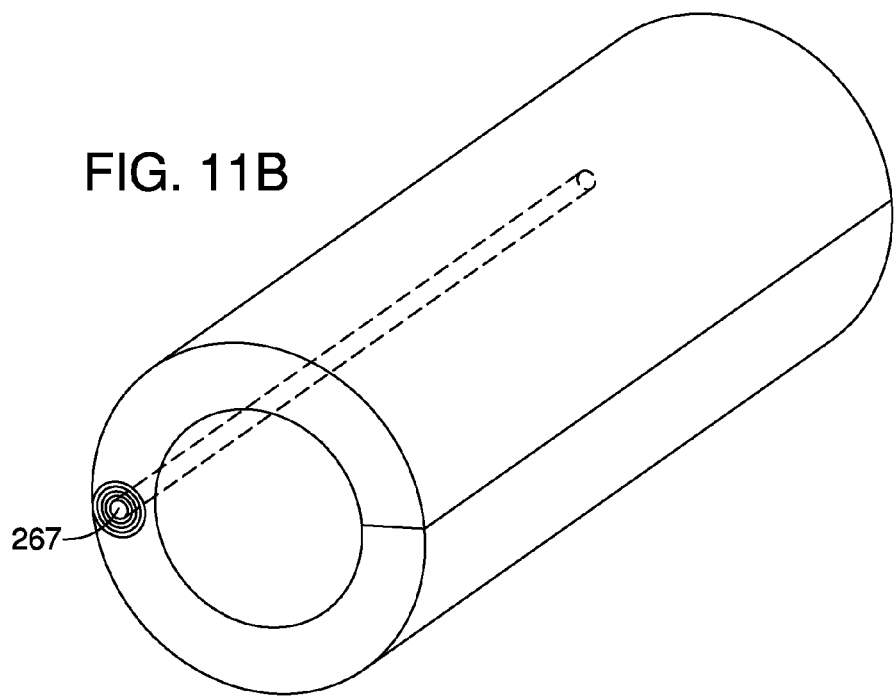
FIG. 11B depicts embodiments of a cuff with a multi-element elastic member installed.
Figures 12A, 12B, 12C:
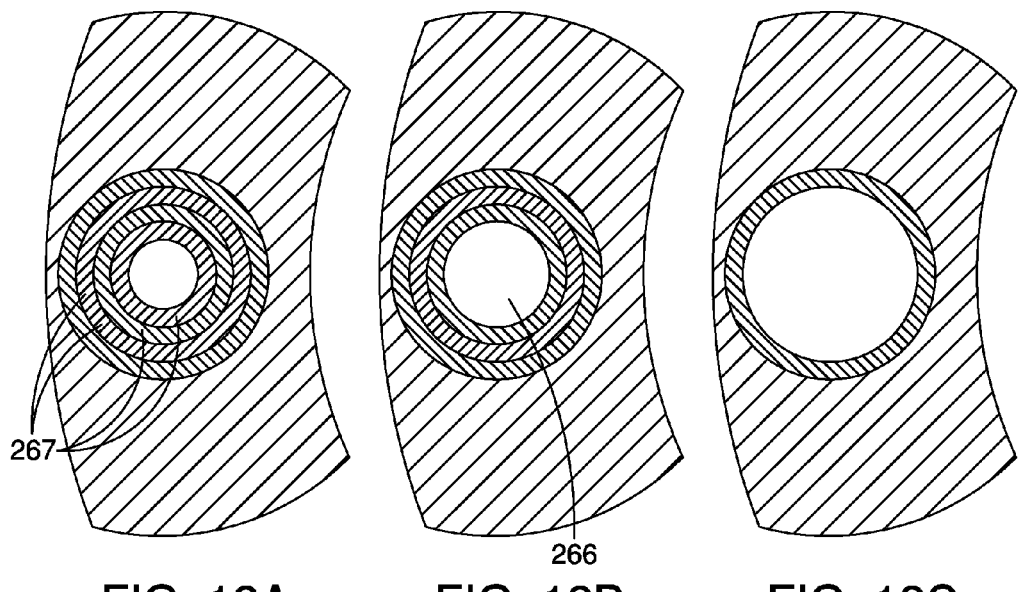
FIGS. 12A-C depict a portion of a cuff with an elastic member comprising various numbers of elements.

In some embodiments, depicted in FIGS. 10A and B, 11A and B, and 12A-C, the elastic hinge 260 includes a hole 266 running substantially the length of the cuff. Into the hole can be inserted one or more elastic members 267. In some embodiments, the elastic members 267 are telescoping such that they can be easily placed in the hole, either as a group of elements or individually. Thus, as shown in FIGS. 12A-C, the elastic hinge 260 can comprises one elastic member 267 or a plurality of the same.

The elastic members 267 can be fashioned from the same material as the cuff or from a different material, depending on the mechanical properties one wishes to impart and/or the nerve diameter to be enclosed. The number of members will likewise be selected based on the desired elastic properties of the cuff, as well as the degree to which one wishes the cuff to resist expansion by an enclosed object. In some embodiments, as shown in FIGS. 13A-D and FIGS. 14 A and B, the elastic hinge comprises a relatively thickened region 268, with a hole 266 located within the interior of the thickened region. Here, increasing the opening angle eventually result in the collapse of the relatively thinner outer wall that defines the hole 266, such that the elastic hinge 260 yields, as best seen by comparing FIGS. 14A and 14B.

The electrodes used in the device can be made from a variety of conductive materials well known in the art. For example, electrodes can be fashioned from, without limitation, metals such as platinum, iridium, or rhodium or gold, or from any other electrically conductive biologically compatible material. The leads can be made from similar materials to the electrodes, or from any other materials suitable for use in nerve stimulation systems. Typically leads will be insulated to prevent current leakage between the signal generator or IPG and the electrodes. A variety of signal generators or IPGs are also suitable for use with the presently disclosed electrode.

In some embodiments, electrodes can be mounted on the inner surface of the cuff portion of the device such that the electrode is effectively flush with the inner surface of the cuff. In these cases, the electrode will make intimate physical, and hence direct electrical contact with the nerve surface. In some embodiments, it is an advantage to provide electrodes that are recessed with respect to the inner surface of the cuff portion. Studies have shown that recessed electrodes more effectively inject charge, and produce a more uniform electrical field across the surface on the electrode, as compared to those mounted co-planar with the surface of the surrounding matrix holding the electrodes (See, e.g., Suesserman et al., 1991, IEEE 38: 401-408).

Figure 6:
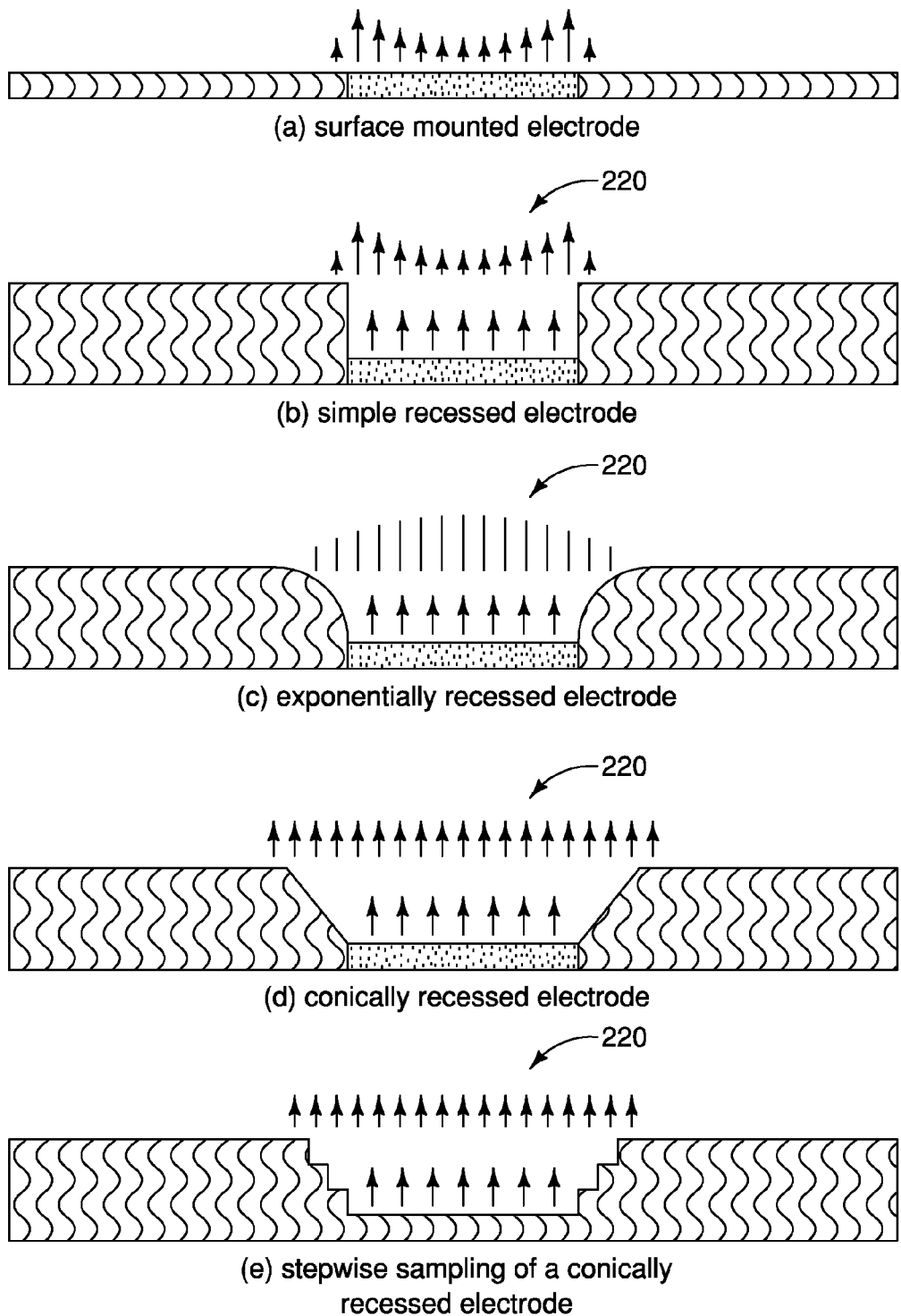
FIG. 6 depicts the effect of recessed electrode placement on charge profile.
Figure 7A:
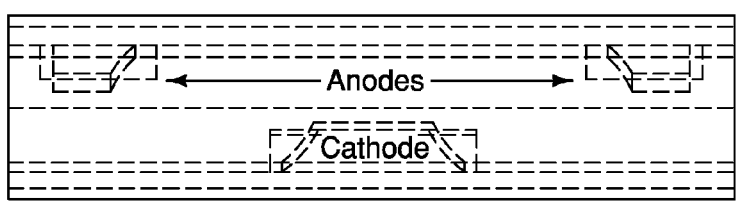
FIGS. 7A-D provide additional views of one embodiment of a self-sizing cuff electrode.
Figure 7C:
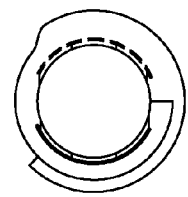
Figure 7B:
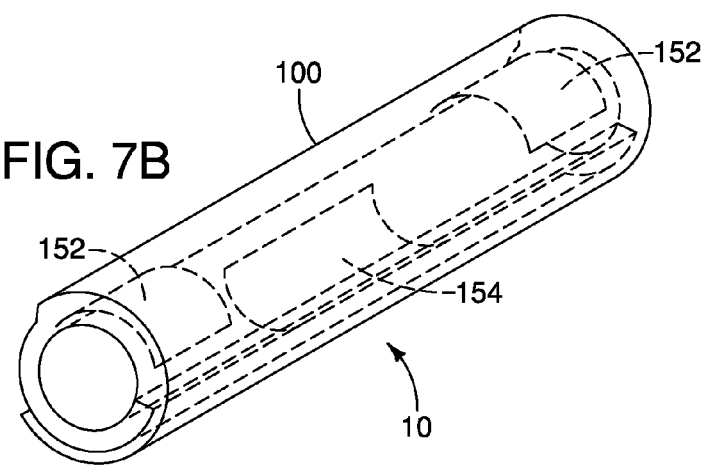
Figure 7D:
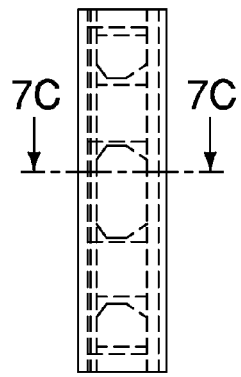
Figure 8:
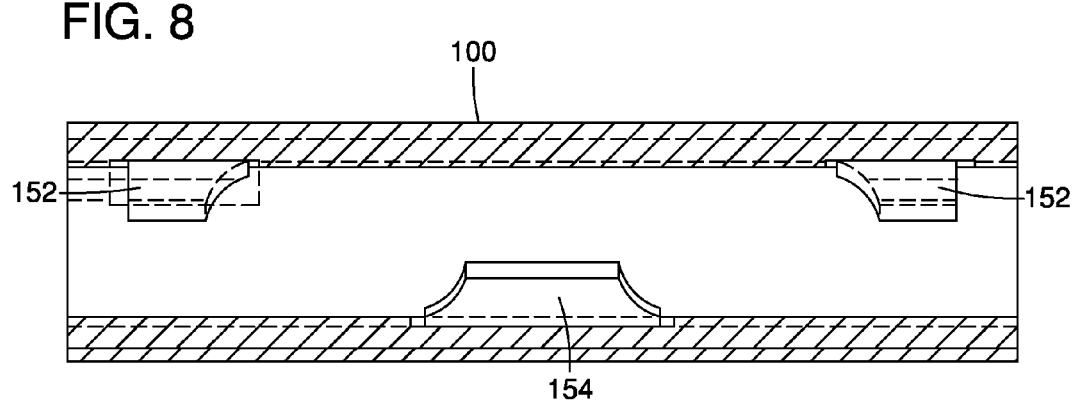
FIG. 8 depicts additional views of one embodiment of a self-sizing cuff.

The recess can comprise walls with varying geometries. For example, in some embodiments a recess is configured such that the walls are effectively perpendicular to the surface of the electrode. In some embodiments, the walls of the recess are exponentially recessed. In some embodiments, the walls of the recess are conically recessed. In some embodiments, the walls are recessed in a stepwise configuration that mimics a conically recessed electrode. Exemplary embodiments of recessed electrodes are depicted in FIG. 6.

In the case of a recessed electrode configuration, conduction between the electrode and the nerve occurs via a conductive material spanning the gap between the electrode surface and the nerve surface. This depth of the recess 220 can vary. In some embodiments, the depth of the recess ranges from about 10% to about 125% of the diameter of the electrode. The conductive material spanning the gap between the electrode surface and nerve surface can comprise any suitable fluid, gel, or even solid that is capable of effective conduction of electrical current from the electrode to the nerve surface. Such materials can include, without limitation, normal saline, electro-conductive gels, and the like. For example, U.S. Pat. No. 5,178,143 to Kwak et al. (the entirety of which is incorporated by reference herein) discloses an electrically conductive gel comprising a cross-linked, neutralized copolymer of maleic anhydride and a C1-C5 alkyl vinyl ether. The conductive material is applied to the recessed region prior to placement of the cuff around the nerve. Sufficient material is applied to prevent the occurrence of air gaps, which could otherwise disrupt or alter the current pathway from the electrode to the nerve.

Figure 15A:
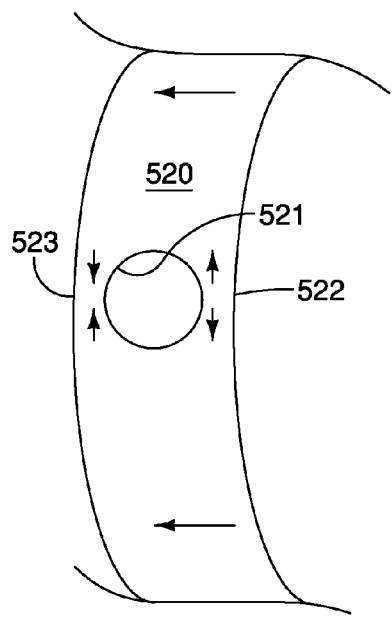
FIGS. 15A-15C illustrates the buckling of hinge regions.

FIG. 15A illustrates a hinge region including a wall 620, a longitudinal lumen 621, and inner wall region 622, and an outer wall region 623. During cuff opening, inner wall region 622 is in tension while outer wall region 623 in is compression, in some embodiments. Outer wall region 623 can fail in compression, and either buckle inward or outward, in various embodiments. In varying embodiments, lumen 621 can be round or oblong, either in the direction of the wall or transverse to the wall circumference.

Figure 15B:
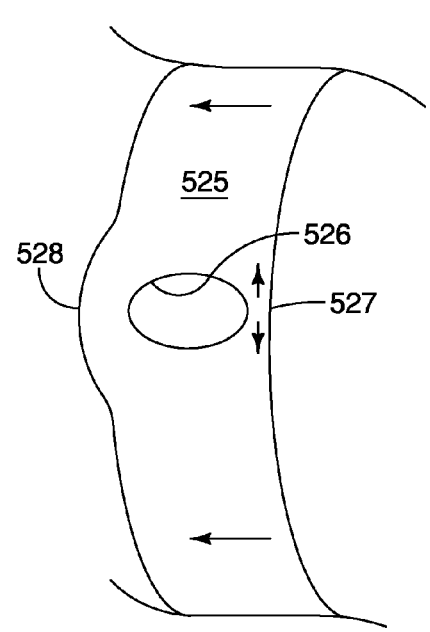
Figure 15C:
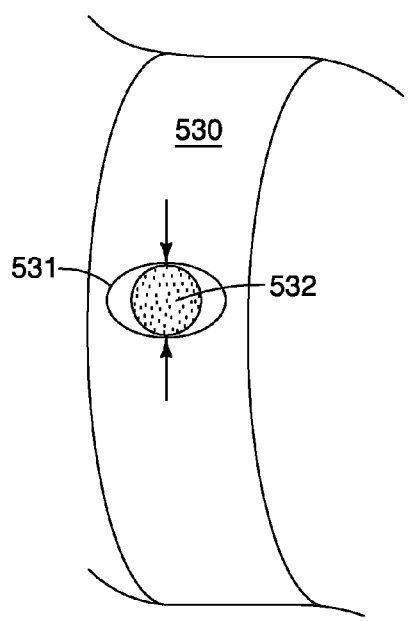

FIG. 15B illustrates another embodiment, having a wall region 625, inner wall region 627, and buckled outer wall region 628, next to lumen 626. FIG. 15C illustrates yet another embodiment, having wall region 630, having compressed lumen 631, having an inner member 632 within. As lumen 626 is further compressed, it can in turn apply compressive forces against inner member 632. Why any gap surrounding the inner member is crossed, the outer forces may eventually cause the inner member to elastically compress and/or fail itself. In this way, the inner member can serve as yet another spring constant which can resist the further opening of the cuff. The inner member can be an elastic solid shaft in some embodiments and a hollow tube in others.

Figure 16:
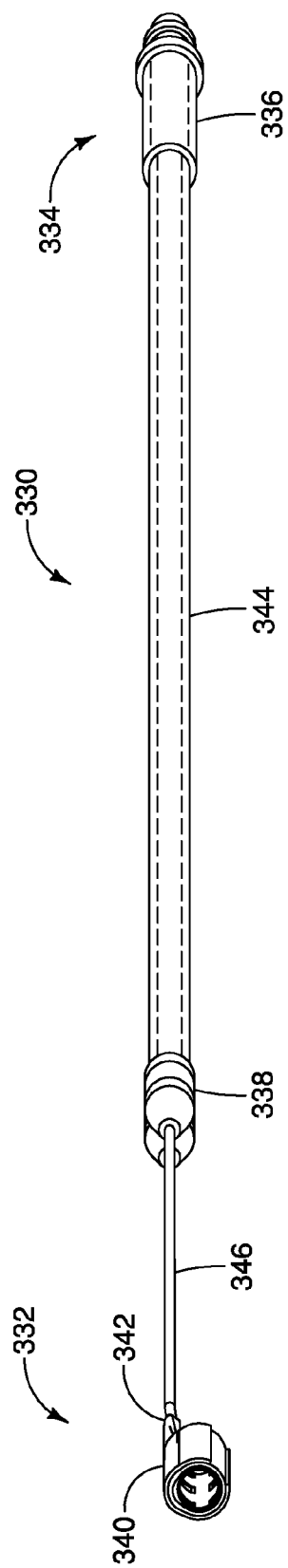
FIG. 16 is a perspective view of a lead according to the present invention, having a proximal connector, an intermediate yoke, and a distal cuff.

FIG. 16 illustrates one embodiment of the invention in a lead 330 having a proximal portion 334 and a distal portion 332. Lead 330 includes a proximal connector 336 which can be an IS1 connector. A proximal lead body 344 extends distally from connector 336 and is coupled to a yoke 338. A distal lead body (or bodies) 346 extends distally from yoke 338 and is coupled to a cuff 340 through a strain relief 342.

In some embodiments, lead 330 proximal lead body 344 includes two electrically insulated conductors which are electrically coupled at yoke 338 to two distal conductors. The proximal conductor can be, for example, an electrically conductive coil having two insulated conductors. Distal lead body 346 can be two distinct insulated wires or cables in some embodiments, and can be joined over their entire lengths or at certain distinct positions by a polymeric substance. The design of lead 330 allows a standard IS1 connector and coupled lead body to be coupled to a set of finer, distal lead conductors. In the embodiment illustrated, proximal lead body 344 is larger and more robust than the finer wires found in the distal lead body 346. In some embodiments, yoke 338 also serves as a suture point for fixing the position of the lead within the human body.

Figure 17:
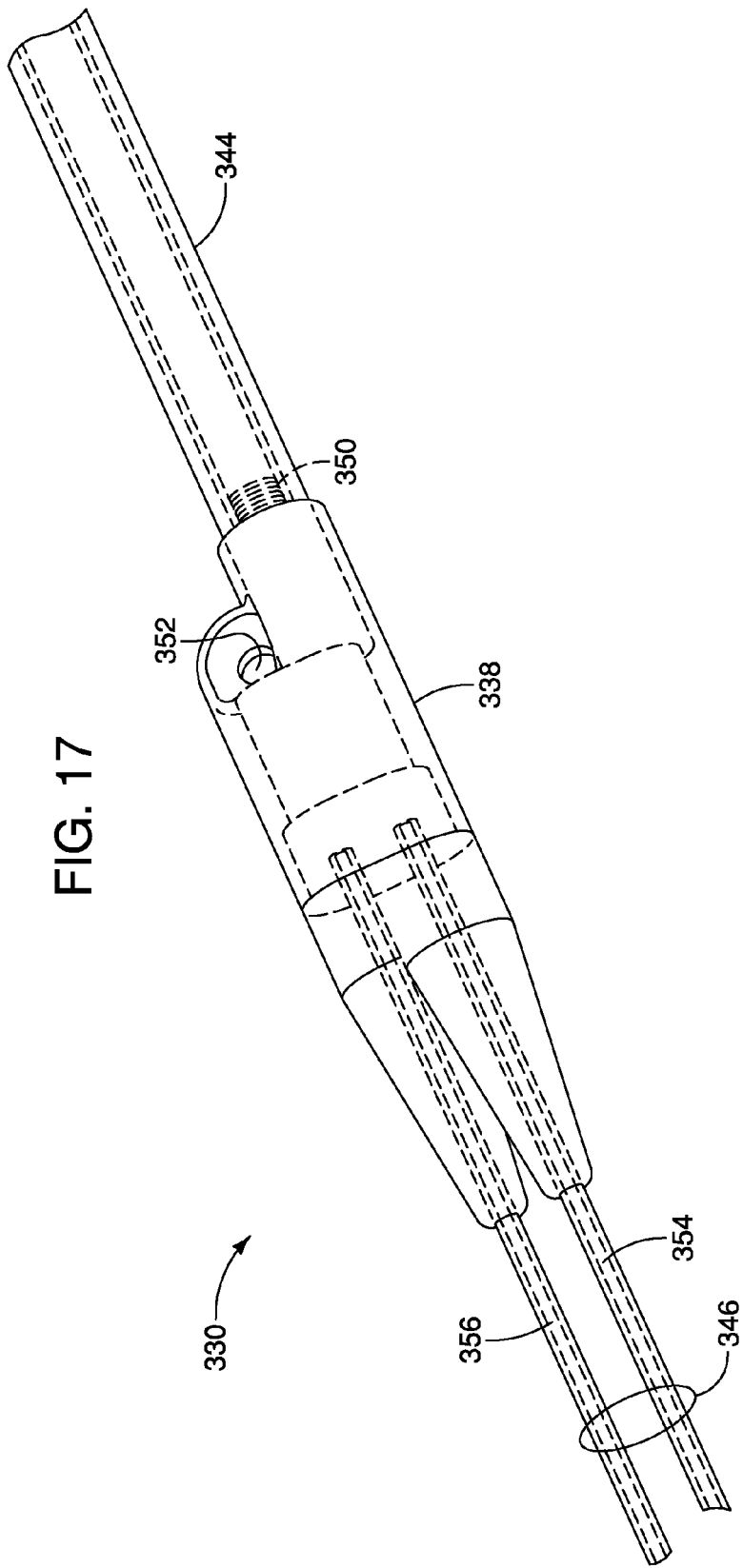
FIG. 17 is a fragmentary, perspective view of the yoke of FIG. 16, connecting a proximal lead body to distal lead bodies.

FIG. 17 illustrates yoke 338 in more detail. Proximal lead body 344 may be seen to include coiled conductors 350 which are electrically coupled within the yoke to two distinct proximal conductor wires 354 and 356, both included within a polymeric body. Yoke 338 can also include a suture hole 352, as illustrated.

Figure 18:
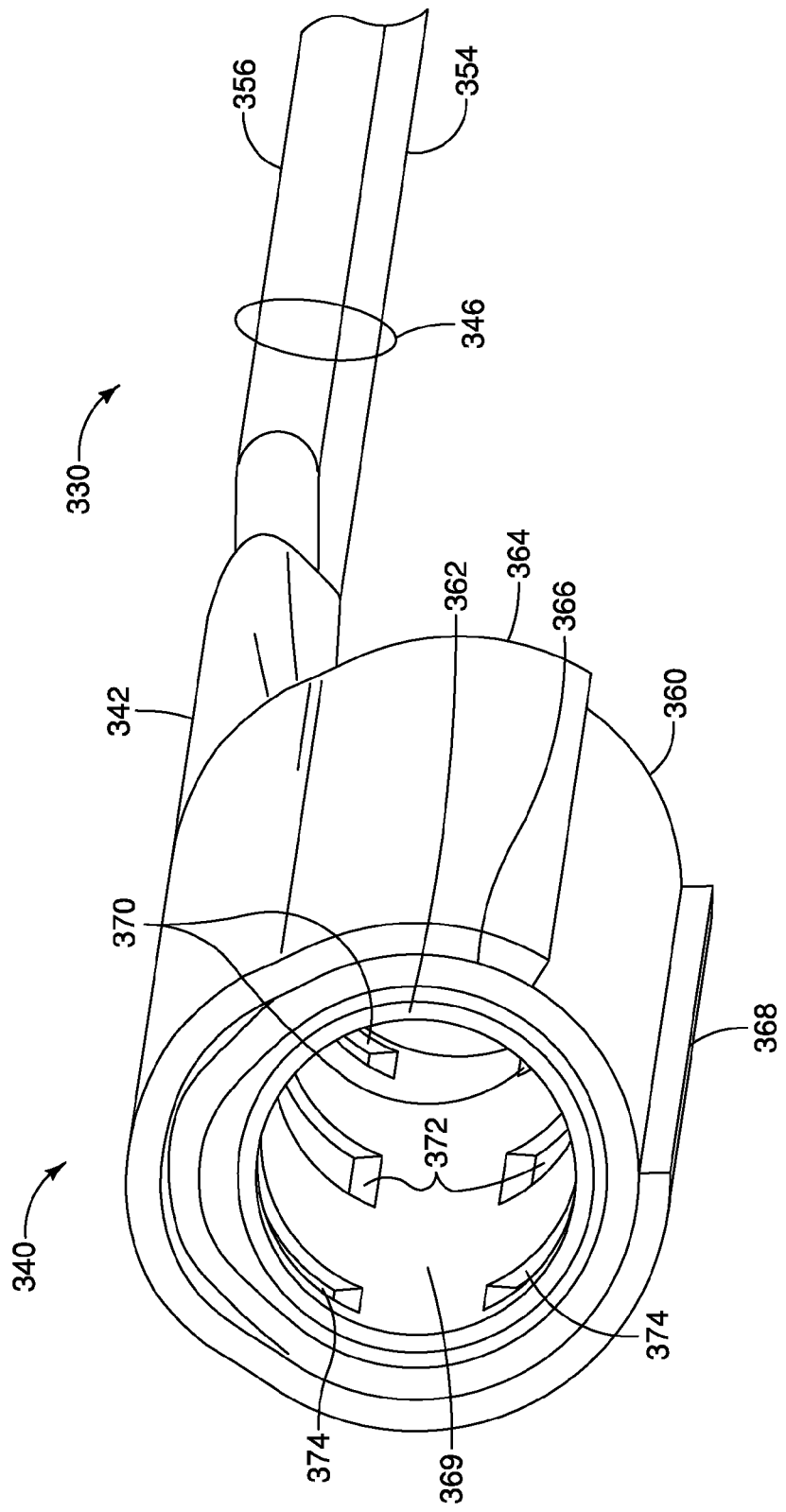
FIG. 18 is a fragmentary, perspective view of a cuff electrode having interior, recessed, conductor plates disposed within a tubular body closed about a slit and having a flap covering the slit and wrapping around the tubular body.
Figure 19:
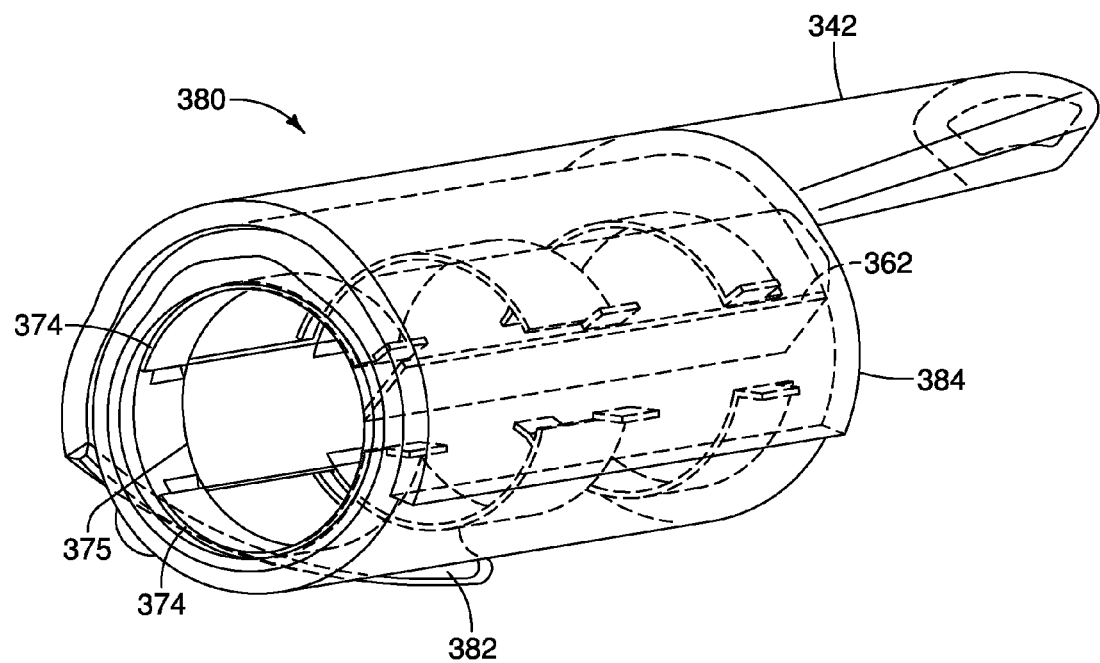
FIG. 19 is a perspective view of a cuff electrode subassembly having a flap with a tapered free edge and jumper wires/springs electrically coupling the curved electrode plates.

FIG. 18 illustrates a cuff 340 having a proximal lead body 346 coupled to strain relief 342. Inspection of FIG. 18 shows a cuff tubular body 360 having a slit 362 therethrough. Slit 362 allows the tubular body to be opened and placed over a nerve. A flap 364 can be secured at flap region 366 to tubular body 360. Flap 364 extends over slit 362 and around a tubular body 360 and terminating in a flap free region 368. In some embodiments, flap free region 368 is tapered. Cuff tubular body 360 has a tube interior region 369 opposite slit 362 and between the conductor plates. In the embodiment illustrated, there are generally opposed distal conductor plates 374, an intermediate pair of conductor plates 372, and proximal conductor plates 370. The conductor plates can be recessed within the tube interior wall, to provide for improved performance. In one embodiment, intermediate conductor plates 372 form the cathode, and distal and proximal conductor plates 374 and 370 form the anodes. In this embodiment cathode 372 is electrically coupled to one elongate conductor, for example, distal conductor 354, while the distal and proximal conductor plates 374 and 370 are coupled to the other distal conductor, for example, distal conductor 356. If flap free region 368 were peeled clockwise and free of tubular body 360, this would open the tubular body about slit 362 and allow nerve cuff 340 to be placed over a nerve. FIG. 19 illustrates yet another cuff 380, shown as a subassembly not including the lead bodies. Cuff 380 is coupled to strain relief 342. A flap 384 may be seen to wrap around the tubular body and terminate in a free edge tapered flap 382. The free edge tapered flap can provide a more suitable leading edge for inserting under a nerve in a body. The pair of opposed distal recessed conductor plates 374 may be seen in FIG. 19. A distal jumper wire or spring 375 may also be seen in this embodiment, located opposite of slit 362 in the tubular body.

Figure 20:
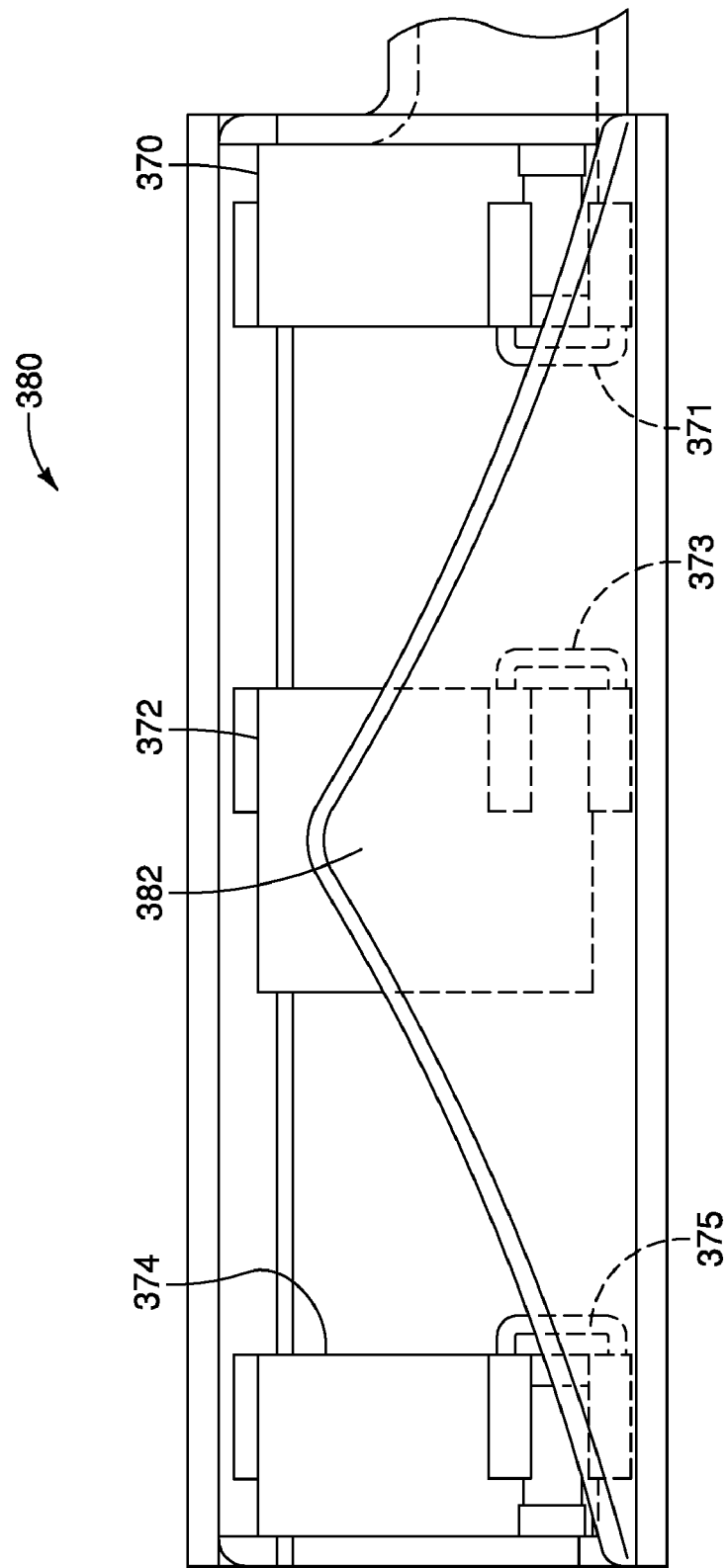
FIG. 20 is a side view of the cuff of FIG. 19, better illustrating the jumper wires/springs coupling the curved electrode plates.

FIG. 20 again illustrates cuff 380 of FIG. 19, from the side. The free or leading a flap edge 382 is shown as are center curved electrode plates 372, the proximal curved electrode plates 370, and the distal electrode plates 374. Jumper wires or springs 371, 373, and 375 may also be seen.

Figure 21:
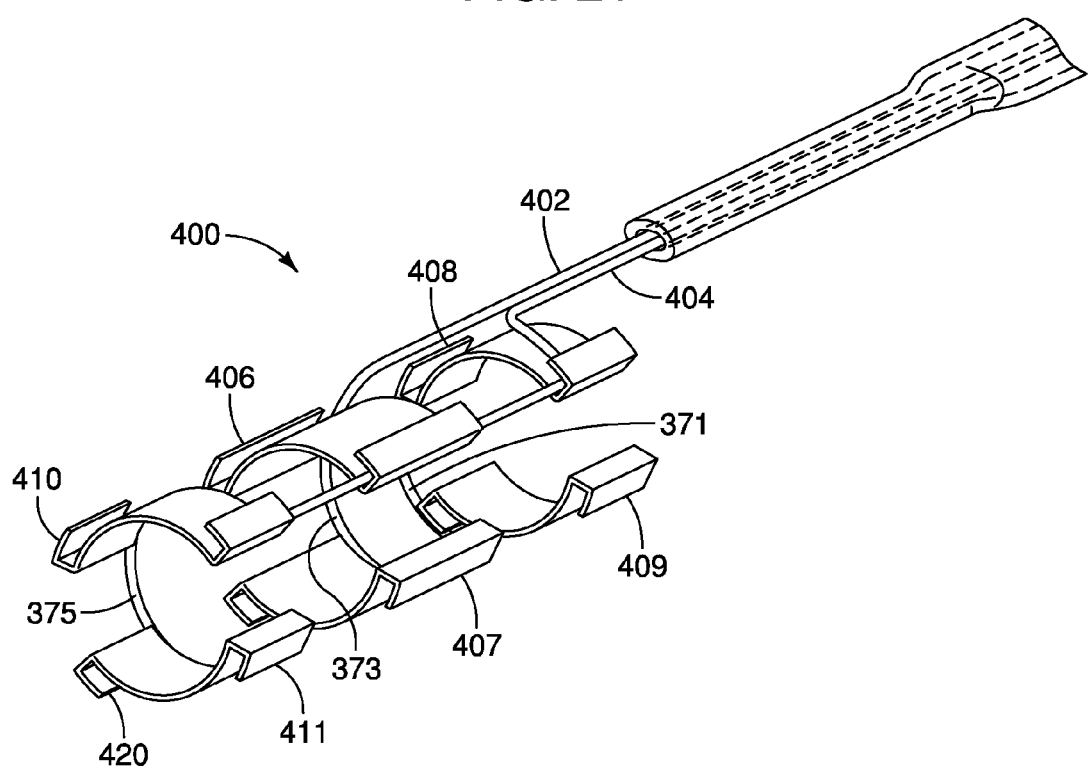
FIG. 21 is a fragmentary, perspective view of a cuff electrode subassembly better illustrating the opposed, curved plate electrodes and the conductor wires coupled to the plates.

FIG. 21 illustrates a cuff subassembly 400 including a first or anode conductor wire 402 coupled through a weld tube to top cathode curved plate 406. Jumper wire or spring 373 may be seen to electrically couple the first or top cathode plate 406 to the bottom or second cathode plate 407. A second conductor or cathode wire 404 may be seen electrically coupled through a weld tube or otherwise welded to the proximal, top curved electrode plate 408. Second conductor or cathode wire 404 extends past the middle cathode plate and couples to the distal, top curved cathode plate 410. Top, proximal plate 408 is coupled through a jumper wire or spring 371 to the bottom proximal conductor plate 409. Similarly, the distal conductor top plate 410 is electrically coupled through a jumper wire or spring 375 to the bottom conductor plate 411.

The middle conductor plates 406 and 407 are illustrated as longer than each of the other plates. In one embodiment, the cathode has a surface area about twice that of each of the adjacent anode curved conductor plates. The total cathode surface area is equal to the total anode surface area is some embodiments. In one embodiment, both anode plates are spaced the same at distance from the middle cathode plate. This means that, for example, distal conductor plates 410 and 411 are the same distance from plates 406 and 407 as are plates 408 and 409.

Cuff subassembly 400 also includes a boxed or foldover region 420. This can be used to receive the jumper wires, the weld attachment tubes, and may also function to secure the cuff tubular polymeric body to the conductor plates after the polymer is added.

FIG. 22 again illustrates cuff subassembly 400, in greater detail. Curved conductor plates 408, 406, and 410 are shown as before. The second or cathode conductor wire 404 is coupled to the top cathode plate 406 through a weld attachment tube, with the conductor wire terminating at 428. Weld attachment tube 424 may also be seen. In some embodiments, the conductor wire is inserted within the tube and laser welded to the tube. The tube can then be laser welded to the curved electrode plate. Conductor jumper wire 373 can be also laser welded to weld tubes and the jumper wire bent into a curve shape on a bending jig. This subassembly can then be inserted into the folded over region of the cathode curved conductor plates and then laser welded to each of the conductor plates. Similarly, the other elongate conductor wire 402 can be electrically and physically coupled through a weld to the anode curved electrode plates 408 and 410. This again can be performed through the weld tubes previously discussed. In some embodiments, the curved electrode plates are formed of platinum iridium alloy, which can be about 0.001 inch in thickness. The jumper wires can be formed of MP35N material, which can be about 0.0065 inch OD in some embodiments. The weld tubes can be formed of stainless steel in some embodiments. In some embodiments, the jumper wires and conductor wires are laser welded more toward the free end of the jumper wire or conductor wire within the weld tube. Referring again to FIG. 22, the curved plate electrodes have fold over regions 120. The conductor plates also have mooring slots 421 and mooring holes 426. During manufacture, when molten or pre-polymer solution is infused over the curved plates and jumper wires, the material can flow at least partially into the holes and slots and provide polymeric anchoring points for the structure.

In some embodiments of the invention, the jumper wires, for example, jumper wire 373 provides little in the way of mechanical structural support of the finished cuff. In this embodiment, the jumper wires neither substantially inhibit nor bias the opposed curved plates to open or close about the nerve. In another embodiment, the jumper wires can provide a spring like a function to the overall cuff. In this embodiment, the jumper wires can function as springs which serve to urge the opposed plate electrodes back together when the electrodes are splayed far apart. In one such embodiment, the polymeric material forming the cuff has an elastic, non-linear spring constant such that the polymeric material provides a stronger closing force when the cuff is nearly closed and a weaker closing force as the cuff is splayed further and further apart. In such an embodiment, the spring function of the jumper wires can be engineered to have another spring constant which provides lesser force as the opposed plates are splayed further and further apart. Engineered springs are well known to those skilled in the art and can be designed to meet the required criteria. Some types of engineered springs are formed of multiple filars which provide a spring constant. The orientation of the filars and the surrounding structure can be such that the filars are forced into a taller but narrower structure as the two opposed conductor plates are splayed further apart. This increases the thickness of the spring and hence the spring constant as well. Pairing a nonlinear polymeric spring constant which decreases with increasing opening of the cuff; with a nonlinear jumper wire spring constant which increases with increased opening of the cuff effectively creates a linear composite spring function. This composite spring function decreases over most or all of the range of cuff opening in some embodiments. In some embodiments, the jumper wire function is served by different materials which may separately serve the mechanical and electrical properties. E.g. super elastic Nitinol wire having a separate more electrically conductive wire or a coating.

FIG. 23 illustrates cuff 400 of FIG. 22 from the end. Cuff 400 includes anode conductor wire 402, a cathode wire 404, and recessed curved plates 406 and 407, having foldover regions 420. Jumper wire 373 and slit 430 are also illustrated. A polymeric body 423 is generally indicated as well. Inspection of FIG. 23 shows jumper wire 373 enclosed within the polymeric material in the embodiment illustrated. The curved plate electrodes 406 and 407 are facing each other, leaving the sides in between the curved electrodes free of surface electrode material. While jumper wire 373 may function as a weak electrode, this will likely be an insubstantial contribution due to the additional insulating material covering jumper wire 373. As discussed herein, embodiments such as those illustrated in FIG. 22 and FIG. 23 may be said to be substantially free of electrode material opposite the slit, or substantially free of electrode material between the opposed curved electrodes opposite the slit. A cursory inspection of FIG. 22 shows that the surface area of jumper wire 373 contributes very little compared to the surface area of the two opposed curved electrode plates. This, coupled with the added insulation of the polymer in some embodiments decreases further the electrode contribution of the jumper wires.

FIG. 23 also shows that the curved electrode plates are not forced to flex opposite slit 430 as the cuff is opened and shut about the nerve. FIG. 23 shows that the polymeric region opposite slit 430 can be substantially free of metallic material, allowing the polymer to determine the physical properties of this hinge region opposite slit 430. In some embodiments, the durometer of the polymeric material and the material itself can determine the elastic properties of this hinge area. As previously discussed, jumper wire 373 can contribute to the closing force when the cuff is very much open, in some embodiments. In one example of the invention, a 70 D material is used as the polymeric material. Silicone rubber is a polymeric material used in some embodiments.

Figure 24:
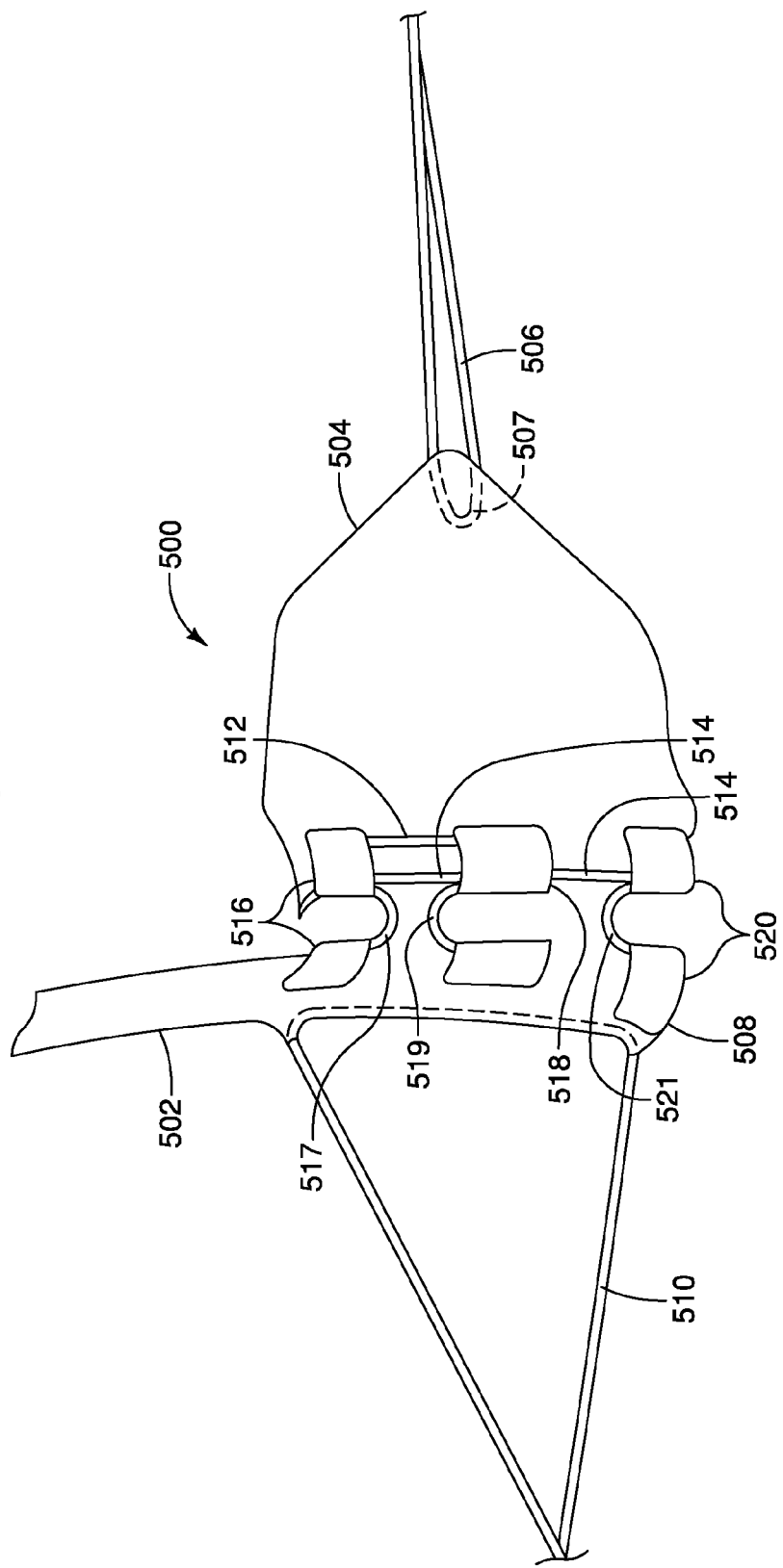
FIG. 24 is a top, photographic view of a nerve cuff pulled apart by the suture loops, showing the opposed curved electrode plates coupled by the jumper wires.

FIG. 24 illustrates a top, a photographic view of one cuff assembly 500 made according to the present invention. FIG. 24 has some edges darkened with a pencil in order to highlight the edges of some features. Cuff assembly 500 includes a strain relief 502, a tapered flap 504, and a suture hole 527 in flap 504, with the flap held open with a suture loop 506. The cuff assembly 500 also includes a second suture 510 pulling at the edge of the tubular cuff. The distal end 508 of the cuff is pulled further apart than the more proximal end of the cuff, a causing the curved plate electrodes to appear larger in the photograph on the distal left side of the cuff. A proximal curved electrode pair 516 is coupled by a jumper wire 517, as is an intermediate curved electrode pair 518 coupled by a jumper wire 519, and a distal curved electrode pair 520 coupled by a jumper wire 521. A first elongate conductor wire 512 is seen coupled to the intermediate electrode pair 518. A second elongate conductor wire 514 is seen electrically coupling proximal electrode pair 516 and distal electrode pair 520. As previously discussed, elongate conductor 512 can be a cathode wire and elongated electrical conductor 514 can be an anode wire, in some embodiments.

FIGS. 25A and 25B illustrate other embodiments of the invention which can provide a tube closing force which varies of the extent of opening of the tube. FIG. 25A illustrates a fragmentary portion of a tubular cuff electrode 600, having a tubular wall portion 602 located substantially opposite the tube slit and between the opposed plates. Tube wall 602 has an interior wall surface 604 and an exterior wall surface 606. In the embodiment illustrated, several wedge shaped slits 608 have been formed into interior wall surface 604. The removal or absence of material can provide a different closing force relative to a similar tube not having the material removed. In one example, the removed material can provide a weaker closing force when the tube is almost entirely closed about the slit. Some embodiments have a single section of material removed or never formed, while other have several sections of material removed.

FIG. 25B illustrates a fragmentary portion of another tubular cuff electrode 610, having a tubular wall portion 612 located substantially opposite the tube slit. Tube wall 612 has an interior wall surface 614 and an exterior wall surface 616. In the embodiment illustrated, several wedge shaped slits 618 have been formed into exterior wall surface 616. The removed or missing material can provide lesser closing force relative to a similar tubular cuff not having the material removed. In yet another embodiment, material sections are removed from both the interior and exterior wall surfaces.

In use, the targeted nerve or nerve bundle can be teased away from surrounding tissue, until the bottom of the nerve is free of the tissue. Then suture loop 506 can be pulled under the nerve, and cuff 500 unwrapped to assume a configuration which may be similar to that shown in FIG. 24. Suture loop 506 can then be pulled under the nerve, followed by tapered flap 504. With the nerve disposed over the electrodes, suture loop 510 can be released, allowing the tubular cuff to close over the nerve body. Suture loop 506 can then be released allowing tapered flap 504 to cover the slit and curl over the now at least partially closed tubular body. The suture loops can then be cut and pulled from the cuff in some embodiments.

Referring again to FIG. 23, another aspect of the invention can be described. In some embodiments, the nerve may be irritated by the surgical manipulation. The nerve may swell slightly or swell later after the nerve cuff is in place. Slit 430 may not be fully closed when the tubular cuff is first placed over the nerve. The opened lead 430 will still preferably be covered by the flap (not shown in FIG. 23). In some embodiments, the curved electrode plates 424 are symmetrical as shown in FIG. 23. In other embodiments, the curved plate electrodes are closer opposite the slit than near the slit. In other embodiments, the curved plate electrodes are closer together near the slit than opposite the slit. In this latter embodiment, the curved plate electrodes can be more nearly symmetrically opposed to each other when the slit is still a part, for example, due to an undersized cuff or a swollen nerve.

The cuff can be manufactured using methods well known to those skilled in the art. In one method, a mandrel or core pin is provided, and the curved plates temporarily adhered to the core pin, for example, you using a cyanoacrylate adhesive. The jumper or wires can be laser welded to the weld tubes and the jumper wire-weld tube assembly can be inserted into the foldover region of the curved electrode plates and the weld tubes laser welded to the curved electrode plates. The elongate conductors to the cathode and anode can also be laser welded to the curved electrode plates, for example, by again using weld tubes. The mandrel or core pin now carrying the curved electrode plates and a jumper wires can be placed in a two-part mold. A molten polymer or a pre-polymeric solution can be infused into the mold. The interior core pin or mandrel can prevent the polymer from flowing too far into the future cuff interior. The interior surface of the mold will prevent the polymer from flowing too far outside of the future cuff. After the polymer has cured or solidified, the interior of the mandrel or core pin can be removed, leaving the cuff assembly. In some methods, the proximal lead bodies can also be formed in this process, for example, formed with the strain relief and the cuff. The cuff subassembly can be coupled to the proximal subassembly.

While the disclosed embodiments have generally been described in the context of contacting a nerve with a self-sizing cuff electrode, there are other physiological application for the device as disclosed. For example, in addition to electrical stimulation of nerves, other tissues can also be subjected to simulation with electrical energy, and in some cases enclosing the tissue in a resilient cuff can provide an advantage. For example, the healing of difficult bone fractures using electrical current or ultrasound is well known. The present cuff and electrode combination can be readily adapted to a scale effective for use in orthopedic applications.

The invention claimed is:

1. A cuff electrode comprising:
a first elongate conductor;
a second elongate conductor;
a first pair of opposed curved electrically conductive plates electrically coupled to each other and to the first conductor;
a second pair of opposed curved electrically conductive plates electrically coupled to each other and to the second conductor;
a third pair of opposed curved electrically conductive plates electrically coupled to each other and to the first conductor, wherein the first, second, and third pairs of curved electrically conductive plates each have an electrically exposed interior surface;
an elongate flexible shaft having a proximal region and a distal region and having the first and second conductors disposed along the shaft;
a flexible curved cuff operably coupled to the shaft distal region, the cuff including a tubular body having an interior region and an exterior region, and having the first, second, and third curved electrically conductive plates operably coupled to the cuff tubular body interior region such that the electrically conductive plate interior conductive surface is electrically exposed within the cuff tubular body interior;
the cuff tubular body includes a tubular body wall having a longitudinal slit therethrough allowing the cuff tubular body to open to expose the cuff tubular body interior, and in which the cuff tubular body is biased to urge the tubular body to close the slit; and
the cuff further includes a generally triangular shaped flap with the base of the triangular shaped flap being the length of the tubular body and the base of the triangular shaped flap secured to the tubular body on a first side of the slit, in which the flap to extend around the tubular body and cover the slit.

2. The cuff as in claim 1, in which the opposed curved electrically conductive plates are electrically coupled to each other through electrically conductive wires.

3. The cuff as in claim 2, in which the electrically conductive wires are biased to urge the opposed plates closer together.

4. The cuff as in claim 1, in which the triangular shaped flap includes a at least one removable flexible member which is adapted to being grasped to pull at least a portion of the triangular shaped flap region under a nerve.

5. The cuff as in claim 4, in which the at least one removable flexible member includes a loop of suture material secured an part of the triangular shaped flap distal the base.

6. The cuff as in claim 1, in which the opposed plates have longitudinal edges near the slit and opposite the slit, and in which the edges near the slit and opposite the slit are disposed about the same distance from the opposing plate respective longitudinal edge when the slit is closed.

7. The cuff as in claim 1, in which the opposed plates have longitudinal edges near the slit and opposite the slit, and in which the edges near the slit are disposed a greater distance from the opposing plate respective edges than the edges opposite the slit, when the slit is closed.

8. The cuff as in claim 1, in which the opposed plates have longitudinal edges near the slit and opposite the slit, and in which the edges near the slit are disposed a lesser distance from the opposing plate respective edges than the edges opposite the slit, when the slit is closed.

9. The cuff as in claim 1, in which the cuff tubular region between the opposed plates and opposite the slit is substantially free of electrode material.

10. The cuff as in claim 9, in which the slit of the cuff has at least about 2 mm Hg closing force at 5 degrees of opening and no greater than about 30 mm Hg at 90 degrees of opening.

11. The cuff as in claim 10, in which the hinge region includes a second element providing closing force, where the second element continues to provide cuff closing force past the first cuff opening limit.

12. The cuff as in claim 9, in which the hinge region includes a first element providing cuff closing force, where the first element substantially decreases in closing force past a first opening limit.

13. The cuff as in claim 9, in which the hinge region includes a weakened region susceptible to folding at a large degree of opening, the hinge region further having an inner wall disposed between the hinge weakened region and an outer wall disposed away from the weakened area and inner wall, such that the first element includes the hinge region outer wall.

14. The cuff as in claim 1, in which the cuff tubular region between the opposed plates and opposite the slit is substantially free of an exposed electrode material.

15. The cuff as in claim 1, in which the cuff tubular region between the opposed plates and opposite the slit is substantially free of an exposed electrode material.

16. The cuff as in claim 2, further including jumper wires coupling the opposed plates that are biased to close the cuff tubular body.

* * * * *